(12) United States Patent
Maggio

(10) Patent No.: US 8,883,728 B2
(45) Date of Patent: Nov. 11, 2014

(54) INTRANASAL ADMINISTRATION OF ACTIVE AGENTS TO THE CENTRAL NERVOUS SYSTEM

(75) Inventor: Edward T. Maggio, San Diego, CA (US)

(73) Assignee: Aegis Therapeutics, LLC, San Diego, CA (US)

( * ) Notice: Subject to any disclaimer, the term of this patent is extended or adjusted under 35 U.S.C. 154(b) by 141 days.

(21) Appl. No.: 12/954,219

(22) Filed: Nov. 24, 2010

(65) Prior Publication Data

US 2011/0129462 A1 Jun. 2, 2011

Related U.S. Application Data

(63) Continuation of application No. 11/931,201, filed on Oct. 31, 2007, which is a continuation-in-part of application No. 11/342,058, filed on Jan. 27, 2006, now abandoned.

(60) Provisional application No. 60/655,809, filed on Feb. 23, 2005.

(51) Int. Cl.

| | | |
|---|---|---|
| A61K 38/18 | (2006.01) | |
| A61K 38/19 | (2006.01) | |
| A61K 38/34 | (2006.01) | |
| A61K 9/00 | (2006.01) | |
| A61K 38/50 | (2006.01) | |
| A61K 51/08 | (2006.01) | |
| A61K 47/34 | (2006.01) | |
| A61K 47/48 | (2006.01) | |
| A61K 47/28 | (2006.01) | |
| A61K 47/26 | (2006.01) | |

(52) U.S. Cl.
CPC .............. *A61K 38/50* (2013.01); *A61K 38/34* (2013.01); *A61K 9/0043* (2013.01); *A61K 51/086* (2013.01); *C07K 2319/30* (2013.01); *A61K 47/34* (2013.01); *A61K 47/48415* (2013.01); *A61K 51/088* (2013.01); *A61K 47/28* (2013.01); *A61K 47/26* (2013.01)
USPC ......... 514/11.7; 514/13.1; 514/17.7; 514/5.9; 514/7.6; 514/8.3; 514/8.4; 514/8.5; 514/8.6; 514/8.8; 514/8.9; 514/9.6

(58) Field of Classification Search
CPC .................................................. A61K 9/0043
USPC ......................................................... 514/11.7
See application file for complete search history.

(56) References Cited

U.S. PATENT DOCUMENTS

| | | |
|---|---|---|
| 4,476,116 A | 10/1984 | Anik |
| 4,866,088 A | 9/1989 | Maurin et al. |
| 5,545,806 A | 8/1996 | Lonberg et al. |
| 5,545,807 A | 8/1996 | Surani et al. |
| 5,569,825 A | 10/1996 | Lonberg et al. |
| 5,578,567 A | 11/1996 | Cardinaux et al. |
| 5,591,669 A | 1/1997 | Krimpenfort et al. |
| 5,661,130 A | 8/1997 | Meezan et al. |
| 5,830,853 A | 11/1998 | Backstrom et al. |
| 5,856,298 A | 1/1999 | Strickland |
| 5,955,422 A | 9/1999 | Lin |
| 6,715,485 B1 | 4/2004 | Djupesland |
| 6,734,427 B1 | 5/2004 | Tsou et al. |
| 6,750,324 B1 | 6/2004 | Schenk et al. |
| 6,761,888 B1 | 7/2004 | Schenk |
| 6,824,762 B2 | 11/2004 | Haslwanter et al. |
| 6,824,780 B1 | 11/2004 | Devaux et al. |
| 2003/0072793 A1 | 4/2003 | Frey et al. |
| 2004/0028613 A1 | 2/2004 | Quay |
| 2004/0115135 A1 | 6/2004 | Quay |
| 2009/0318353 A1* | 12/2009 | Lau et al. .......... 514/12 |

FOREIGN PATENT DOCUMENTS

| | | |
|---|---|---|
| WO | WO 91/07947 A1 | 6/1991 |
| WO | WO 96/22802 A1 | 8/1996 |
| WO | WO 9717852 A1 | 5/1997 |
| WO | WO 98/30207 A1 | 7/1998 |
| WO | WO 00/09073 A2 | 2/2000 |
| WO | WO 00/33813 A1 | 6/2000 |
| WO | WO 00/33814 A2 | 6/2000 |
| WO | WO 01/10912 A1 | 2/2001 |
| WO | WO 01/82902 A1 | 11/2001 |
| WO | WO 2003/072056 A2 | 9/2003 |
| WO | WO 2004/002424 A2 | 1/2004 |
| WO | WO 2006/091332 A2 | 8/2006 |
| WO | WO 2008/049897 A1 | 5/2008 |

OTHER PUBLICATIONS

Agarwal et al., "Recent trends in drug delivery systems: Intranasal drug delivery", *Indian Journal of Experimental Biology*, 37:6-16 (1999).
Alper et al., Intranasal vaccination against plague, tetanus and diphtheria, *Advanced Drug Delivery Reviews*, 51:173-201 (2001).
Baggar et al., "A micro dialysis model to examine nasal drug delivery and olfactory absorption in rats using lidocaine hydrochloride as a model drug", *International Journal of Pharmaceutics*, 269:311-322 (2004).
Bai et al., "Nasal administration of myelin basic protein prevents relapsing experimental autoimmune encephalomyelitis in DA rats by activating regulatory cells expressing IL-4 and TGF-13 mRNA", *Journal of Neuroimmunology*, 80:65-75 (1997).
Bai et al., "Complexities of applying nasal tolerance induction as a therapy for ongoing relapsing experimental autoimmune encephalomyelitis (EAE) in DA rats", *Clinical and Experimental Immunology*, 111(1):205-210 (1998).
Benedict et al., "Intranasal insulin improves memory in humans", *Psychoneuroendocrinology*, 29:1326-1334 (2004).

(Continued)

*Primary Examiner* — Prema Mertz
(74) *Attorney, Agent, or Firm* — DLA Piper LLP (US)

(57) ABSTRACT

Pharmaceutical compositions and methods for delivering a polypeptide to the central nervous system of a mammal via intranasal administration are provided. The polypeptide can be a catalytically active protein or an antibody, antibody fragment or antibody fragment fusion protein. The polypeptides are formulated with one or more specific agents.

6 Claims, 11 Drawing Sheets

(56) References Cited

OTHER PUBLICATIONS

Bodey et al., "Survivin Expression in Childhood Medulloblastomas: A Possible Diagnostic and Proanostic Marker". In Vivo. 18(6):713-718 (2004).

Born et al., "Sniffing neuropeptides: a transnasal approach to the human brain", *Nature Neuroscience*, 5(6):514-516 (2002).

Capsoni et al., "Nerve growth factor and galantamine ameliorate early signs of neurodegeneration in anti-nerve growth factor mice", *Proceedings of the National Academy of Science U.S.A.*, 99(19):12432-12437 (2002).

Catania et al., "Targeting Melanocortin Receptors as Novel Strategy to Control Inflammation", *Pharmacological Reviews*, 56(1):1-29 (2004).

Chen et al., "4- {(2R)-[3-Aminopropionylamido ]-3-(2,4-dichlorophenyl)propionyl} -1-{2-[(2-thienyl)ethienypethylaminomethyl]phenyl}piperazine as a Potent and Selective Melanocortin-4 Receptor Antagonist-Design, Synthesis, and Characterization", *Journal of Medical Chemistry*, 47(27):6821-6830 (2004).

Chen et al., "Delivery of Nerve Growth Factor to the Brain via the Olfactory Pathway", *Journal of Alzheimer's Disease*, 1:35-44 (1998).

Chothia et al., "Canonical Structures for the Hypervariable Regions of Immunoglobulins", *Journal of Molecular Biology*, 196:901-917 (1987).

Comford et al., "New systems for delivery of drugs to the brain in neurological disease", *The Lancet*, 1(5):306-315 (2002).

Del Guidice et al., "Mucosal Delivery of Vaccines", *Methods*, 19:148-155 (1999).

Derad et al., "intranasal Angiotensin II Directly Influences Central Nervous Regulation of Blood Pressure", *American Journal of Hypertension*, Ltd., 11:971-977 (1998).

Direct Inhaler, Pulmonary & Nasal Drug Delivery, DirectHaler Nasal, http://www.directhaler.com (2005).

Eriksson et al., "The Cholera Toxin-Derived CTAI-DD Vaccine Adjuvant Administered Intranasally Does Not Cause Inflammation of Accumulate in the Nervous Tissue", *The Journal of Immunology*, 173:3310-3319(2004).

Fabian, R.H., "Uptake of antineuronal IgM by CNS neurons: Comparison with antineuronal IoG", *Neurology*, 40:419-422 (1990).

Fabian et al., "Intraneuronal IgG in the central nervous systems: Update by retrograde axonal transport", *Neurology*, 37:1780-1784 (1987).

Falero-Diaz et al., "Transmission of IgA and IgG Monoclonal Antibodies to Mucosal Fluids following Intranasal or Parenteral Delivery", *International Archives of Allergy and Immunology*, 122:143-150 (2000).

Fehm et al., "The Melanocortin Melanocyte-Stimulating Honnone/Adrenocorticotropll$_{4-10}$ Decreases Body Fat in Humans", *The Journal of Clinical Endocrinology & Metabolism*, 86(3):1144-1148 (2001).

Frenkel, et al., "Filamentous phage as vector-mediated antibody delivery to the brain", *Proceedings of the National Academy of Science U.S.A.*, 99(8):5675-5679 (2002).

Freidlinger et al., "Design and Synthesis of Novel Bioactive Peptides and Petidomimetics", *Journal of Medicinal Chemistry*, 46(26):5553-5566 (2003).

Frey et al., "Intranasal Delivery of wl-Labeled nerve Growth Factor to the Brain via the Olfactory Route", Research Advances in Alzheimer's Disease and Related Disorders, John Wiley and Sons, Ltd., Chapter 37:329-335 (1995).

Frey et al., "Delivery of $^{125}$I-NGF to the Brain via the Olfactory Route", *Drug Delivery*, 4:87-92 (1997).

Frey, William H., Drug Delivery Technology, "Articles: Bypassing the Blood-Brain Barrier to Deliver Therapeutic Agents to the Brain and Spinal Cord", (2002).

Gokulan et al., "Increase in the Immunogenicity of HI V Peptide Antigens by Chemical Linkage to Polytuftsin (TKPR$_{40}$)", *DNA and Cell Biology*, 18(8):623-630 (1999).

Goodman et al., "Peptidomimetic building blocks for drug discovery: An overview", *Pure & Applied Chemistry*, 68(6):1303-1308 (1996).

Gozes, I., "Neuroprotective peptide drug delivery and development: potential new therapeutics", *TRENDS in Neurosciences*, 24(12):700-705 (2001).

Guerrero et al., "Recombinant Norwalk Virus-Like Particles Administered Intranasally to Mice Induce Systemic and Musocal (Fecal and Vaginal) Immune Responses", *Journal of Virology*, 75(20):9713-9722 (2001).

Hallschmid et al., "Manipulating central nervous mechanisms of food intake and body weight regulation by intranasal administration of neuropeptides in man", *Physiology & Behavior*, 83:55-64 (2004).

Harlow, D. and Lane E., Using Antibodies: A Laboratory Manual, Cold Springs Harbor Laboratory Press, Woodbury, NY (1998); and Subramanian, G., Antibodies: Production and Purification, Kluwer Academic/Plenum Publishers, New York, NY (2004).

Henderson "Role of neurotrophic factors in neuronal development", *Current Opinion in Neurobiology*, 6: 64-70 (1996).

Hoogenboom et al., "By-passing Immunization: Human Antibodies from Synthetic Repertoires of Gennline $V_H$ Gene Segments Rearranged in Vitro", *Journal of Molecular Biology*, 227:381-388 (1992).

Illum, L., "Transport of drugs from the nasal cavity to the central nervous system", *European Journal of Pharmaceutical Sciences*, 11:1-18 (2000).

Illum, L., "Is nose-to-brain transport of drugs in man a reality?" *Pharmacy and Pharmacology*, 56(1):3-17 (2004).

Jakobovits et al., "Germ-line transmission and expression of a human-derived yeast artificial chromosome", *Letters to Nature*, 362:255-258 (1993).

Jakobovits et al., "Analysis of homozygous mutant Chimeric mice: Deletion of the immunoglobulin heavy-chain joining region blocks B-cell development and antibody production", *Proceedings of the National Academy of Science*, 90:2551-2555 (1993).

Jarolim et al., "The role of blood vessels and lungs in the dissemination of *Naegleria fowleri* following intranasal inoculation in mice", *Folia Parasitologica*, 49:183-188 (2002).

Jones et al., "Replacing the complementarity-determining regions in a human antibody with those from a mouse", *Nature*, 321:522-525 (1986).

Joshi et al., "Interleukin-13 Receptor a Chain: A Novel Tumor-associated Transmembrane Protein in Primary Explants of Human Malignant Gliomas", *Cancer Research*, 60:1168-1172 (2000).

Kaushansky et al., "Hematopoietic Growth Factor Mimetics", *Annals New York Academy of Sciences*, 938:131-138 (2001).

Kessler et al, "Identification of the Putative Brain Tumor Antigen BF7/GE2 as the (De)Toxifying Enzyme Microsomal Epoxide Hydrolase", *Cancer Research*, 60:1403-1409 (2000).

Kohler et al., "Derivation of specific antibody-producing tissue culture and tumor lines by cell fusion", *European Journal of Immunology*, 6:511-519 (1976).

Kolar and Capra, Fundamental Immunology, W. E. Paul, ed., Raven Press, N. Y., Chapter pp. 47-68 (1993).

Korner et al., the emerging science of body weight regulation and its impact on obesity treatment, *Journal of Clinical Investigation*, 111:565-570 (2003).

Kucheryanu et al., "Intranasal Fibroblast Growth Factors Delivery into the Brain Exerts Antiparkinsonian Effect in Mice", *Proceedings of the International Symposium Controlled Release Bioactive Materials*, 26:643-644 (1999).

Lavelle et al., "The identification of plant lectins with mucosal adjuvant activity", *Immunology*, 102:77-86 (2001).

Lemiale et al., "Enhanced Mucosal Immunoglobulin A response of Intranasal Adenoviral Vector Human Immunodeficiency Virus Vaccine and Localization in Central Nervous System", *Journal of Virology*, 77(18):10078-10087 (2003).

Liu et al., "Intranasal administration of insulin-like growth factor-I bypasses the blood-brain barrier and protects against focal cerebral ischemic damage", *Journal of the Neurological Sciences*, 187:91-97 (2001).

Marks et al., "By-passing Immunization: Human Antibodies from V-gene Libraries Displayed on Phage", *Journal of Molecular Biology*, 222:581-597 (1991).

(56) References Cited

OTHER PUBLICATIONS

Mathison et al., "Nasal Route for Direct Delivery of Solutes to the Central Nervous System: Fact or Fiction?" *Journal of Drug Targeting*, 5(6):415-441 (1998).
Minn et al., "Drug Transport into the Mammalian Brain: The Nasal Pathway and its Specific Metabolic Barrier", *Journal of Drug Targeting*, 10(4):285-296 (2002).
Nabavi et al., "CT Assessment of Cerebral Perfusion: Experimental Validation and Initial Clinical Experience", *Radiology*, 213:141-149 (1999).
Navarro et al., "MTII-induced reduction of voluntary ethanol drinking is blocked by pretreatment with AgRP-83-132)", *Neuropeptides*, 37:338-344 (2003).
OptiNose Technology, "Drug Delivery Technology", http://www.optinose.no/technology (2005).
Pardridge, W.M., "Drug and Gene Targeting to the Brain with Molecular Trojan Horses", *Nature Reviews*, 1:131-139 (2002).
Pardridge, W.M., "Blood-Brain Barrier Drug Targeting: The Future of Brain Drug Development", *Molecular Interventions*, 3(2):90-105 (2003).
Perlman et al., "Spread of MHV-JHM from Nasal Cavity to White Matter of Spinal Cord", *Advances in Experimental and Medical Biology*, 380:73-78 (1995).
Pietrowsky, et al., "A Nose-Brain Pathway for Psychotropic Peptides: Evidence From a Brain Evoked Potential Study with Cholecystokinin", *Psychoneuroendocrinology*, 21(6):559-572 (1996).
Pietrowsky et al., "Brain Potential Changes after Intranasal vs. Intravenous Administration of Vasopressing: Evidence for a Direct Nose-Brain Pathway for Peptide Effects in Humans", *Biological Psychiatry*, 39:332-340 (1996).
Reichmann et al., "Reshaping human antibodies for therapy", *Nature*, 332: 323-327 (1988).
Ripka, et al., "Peptidomimetic design", *Current Opinion in Chemical Biology*, 2:441-452 (1998).
Ross et al., "Intranasal administration of interferon beta bypasses the blood-brain barrier to target the central nervous system and cervical lymph nodes: a non-invasive treatment strategy for multiple sclerosis", *Journal of Neuroimmunology*, 151:66-77 (2004).
Sakane et al., "Direct Drug Transport from the Rat Nasal Cavity to the Cerebrospinal Fluid: the Relation to the Molecular Weight of Drugs", *Journal of Pharmacy and Pharmacology*, 47:379-381 (1995).
Sakane et al., "The Transport of a Drug to the Cerebrospinal Fluid Directly from the Nasal Cavity: The Relation to the Lipophilicity of the Drug", *Chemical and Pharmaceutical Bulletin*, 39(9):2456-2458 (1991).
Sakane et al., "Direct drug transport from the rat nasal cavity to the cerebrospinal fluid: the relation to the dissociation of the drug", *Journal of Pharmaceutical Pharmacology*, 46:378-379 (1994).
Scarcella et al., "Expression of MAGE and GAGE in High-Grade Brain Tumors: A Potential Target for Specific Immunotherapy and diagnostic Markers", *Clinical Cancer Research*, 5:335-341 (1999).
Schulz et al., "Central Nervous and Metabolic Effects of Intranasally Applied Leptin", *Endocrinology*, 145:2696-2701 (2004).
Scott et al., "Solid-Phase Synthesis of Constrained Terminal and Internal Lactam Peptidomimetics", *Organic Letters*, 6(10):1629-1632 (2004).
Sedlik et al., "Intranasal Delivery of Recombinant Parvovirus-Like Particles Elicits Cytotoxic T-Cell and Neutralizing Antibody Responses", *Journal of Virology*, 73(4):2739-2744 (1999).
Shardonofsky et al., "Therapeutic efficacy of an anti-IL-5 monoclonal antibody delivered into the respiratory tract in a murine model of asthma", *Journal of Allergy and Clinical Immunology*, 104:215-221 (1999).
Sigma, Product Information, *Nerve Growth Factor-2.5S (NGF-2.5S) From Mouse Submaxillary Glands*, Product No. N 6009 (1998).
Sigma, Product Information, *Nerve Growth Factor-Beta (NGF-β) Human, Recombinant, Expressed in NSO Mouse Myeloma Cells*, Product No. N 1408 (2002).
Sigma, Product Information, *Nerve Growth Factor-Beta (NGF-~) Rat, Recombinant, Expressed in Sf Insect Cells*, Product No. N 2513 (2003).
Sims et al., "A Humanized CD18 Antibody Can Block Function without Cell Destruction", *The Journal of Immunology*, 151:2296-2308 (1993).
Singh et al., "A novel bioadhesive intranasal delivery system for the inactivated influenza vaccines", *Journal of Controlled Release*, 70:267-276 (2001).
Snider et al., "Intranasal antigen targeting to MHC class II molecules primes local IgA and serum IgG antibody responses in mice", *Immunology*, 90:323-329 (1997).
Stevenson et al., "The epithelial tight junction: Structure, function and preliminary biochemical characterization", *Molecular and Cellular Biochemistry*, 83:129-145 (1988).
Thompson et al., "Peptoid Mimics of Agouti Related Protein", *Bioorganic & Medicinal Chemistry Letters*, 13:1409-1413 (2003).
Thorne et al., "Delivery of insulin-like growth factor-I to the rat brain and spinal cord along olfactory and trigeminal pathways following intranasal administration ", *Neuroscience*, 127(2):481-496 (2004).
Thorne et al., "Quantitative analysis of the olfactory pathway for drug delivery to the brain", *Brain Research*, 692:278-282 (1995).
Thorne et al., "Delivery of Neurotrophic Factors to the Central Nervous System", *Clinical Pharmacokinetics*, 40(12):907-946 (2001).
Thorne et al., *Society for Neuroscience*, 26:Abstract 511.18 (2000).
Tumpey et al., "Mucosal Delivery of Inactivated Influenza Vaccine Induces B-Cell-Dependent Heterosubtypic Cross-Protection against Lethal Influenza A H5N Virus Infection", *Journal of Virology*, 75(11):5141-5150 (2001).
Vandevyver et al., "Purification of Antibodies by Chromatographic Methods", *Kluwer Academic/Plenum Publishers*, Chapter 5:133-168 (2004).
Verhoeyen et al., "Reshaping Human Antibodies: Grafting an Antilysozyme Activity", *Science*, 239:1534-1536 (1988).
Weltzin et al., "Intranasal Antibody Prophylaxis for Protection against Viral Disease", *Clinical Microbiology Reviews*, 12(3):383-393 (1999).
Winter et al., "Man-made Antibodies", *Nature*, 349:293-299 (1991).
Winter et al., "Making Antibodies by Phage Display Technology", *Annual Review of Immunology*, 12:433-455 (1994).
Wong, "Chemistry of Protein Conjugation and Cross-Linking", *CRC Press*, Boca Raton, FL, Chapter 3:49-73 (1991).
Wrighton et al., "Small Peptides as Potent Mimetics of the Protein Hormone Erythropoietin," *Science*, 273:458-450 (1996).
Xu et al., "Combined Nasal Administration of Encephalitogenic Myelin Basic Protein Peptide 68-86 and IL-I 0 Suppressed Incipient Experimental Allergic Encephalomyelitis in Lewis Rats", *Clinical Immunology*, 96(3):205-211 (2000).
Zhang et al., "Stereoselective Synthesis of Novel Dipeptide β-Turn Mimetics Targeting Melanocortin Peptide Receptors," Organic Letters: 5(17): 3115-3118 (2003).

* cited by examiner

INTRANASAL ADMINISTRATION OF ACTIVE AGENTS TO THE CENTRAL NERVOUS SYSTEM

CROSS-REFERENCE TO RELATED APPLICATIONS

This application claims the benefit of U.S. Provisional Application No. 60/655,809, filed Feb. 23, 2005 and U.S. Utility application Ser. No. 11/342,058 filed Jan. 1, 2006, and U.S. Utility application Ser. No. 11/931,201 filed Oct. 31, 2007 each of which are incorporated herein by reference in their entirety.

TECHNICAL FIELD

The subject matter described herein relates to methods and compositions for intranasal administration of active agents to the central nervous system of a mammal.

BACKGROUND

Delivery of drugs to the central nervous system (CNS) remains a challenge, despite recent advances in drug delivery and knowledge of mechanisms of delivery of drugs to the brain. For example, CNS targets are poorly accessible from the peripheral circulation due to the blood-brain barrier (BBB), which provides an efficient barrier for the diffusion of most, especially polar, drugs into the brain from the circulating blood. Attempts to circumvent the problems associated with the BBB to deliver drugs to the CNS include: 1) design of lipophilic molecules, as lipid soluble drugs with a molecular weight of less than 600 Da readily diffuse through the barrier; 2) binding of drugs to transporter molecules which cross the BBB via a saturable transporter system, such as transferrin, insulin, IGF-1, and leptin; and 3) binding of drugs to polycationic molecules such as positively-charged proteins that preferentially bind to the negatively-charged endothelial surface (See, e.g., Illum, *Eur. J. Pharm. Sci.* 11:1-18 (2000) and references therein; W. M. Partridge. "Blood-brain barrier drug targeting: the future of brain drug development", *Mol Interv.* 3(2):90-105 (2003); W. M. Partridge et al., "Drug and gene targeting to the Brain with molecular Trojan horses", *Nature Reviews-Drug Discovery* 1:131-139 (2002)).

The intranasal route has been explored as a non-invasive method to circumvent the BBB for transport of drugs to the CNS. Although intranasal delivery to the CNS has been demonstrated for a number of small molecules and some peptides and smaller proteins, there is little evidence demonstrating the delivery of protein macromolecules to the CNS via intranasal pathways, presumably due to the larger size and varying physico-chemical properties unique to each macromolecule or class of macromolecules, that may hinder direct nose-to-brain delivery.

The primary physical barrier for intranasal delivery is the respiratory and olfactory epithelia of the nose. It has been shown that the permeability of the epithelial tight junctions in the body is variable and is typically limited to molecules with a hydrodynamic radius less than 3.6 A; permeability is thought to be negligible for globular molecules with a radius larger than 15 A (B. R. Stevenson et al., *Mol. Cell. Biochem.* 83, 129-145 (1988)). Therefore, the size of the molecule to be administered is considered an important factor in achieving intranasal transport of a macromolecule to the central nervous system. Fluorescein-labeled dextran, a linear molecule having a dextran molecular weight of 20 kD can be delivered to cerebrospinal fluid from the rat nasal cavity, however 40 kDa dextran cannot (Sakane et al, *J. Pharm. Pharmacol.* 47, 379-381 (1995)). It has also been reported that an infectious organism, such as a virus, can enter the brain through the olfactory region of the nose (S. Perlman et al., *Adv. Exp. Med. Biol.,* 380:73-78 (1995)).

In published delivery studies to date, intranasal delivery efficiency to the CNS has been very low and the delivery of large globular macromolecules, such as antibodies and their fragments, has not been demonstrated. Yet, because antibodies, antibody fragments, and antibody fusion molecules are potentially useful therapies for treating disorders having a CNS target, e.g., Alzheimer's disease, Parkinson's disease, multiple sclerosis, stroke, epilepsy, and metabolic and endocrine disorders, it is desirable to provide a method for delivering these large macromolecules to the CNS non-invasively.

BRIEF SUMMARY

An aspect of the invention is a pharmaceutical composition comprising a catalytically active peptide chain or a peptide chain comprising an antibody Fc or Fab fragment; and a permeation enhancer in a concentration sufficient to enhance intranasal administration of the catalytically active peptide chain or peptide chain comprising an antibody Fc or Fab fragment to the central nervous system of an animal.

Another aspect of the invention is a pharmaceutical composition comprising a catalytically active peptide chain or a peptide chain comprising an antibody Fc or Fab fragment; and about 0.1 to about 1 g of chitosan glutamate per 100 ml of the pharmaceutical composition; wherein the diluent is an aqueous buffer at standard state.

Another aspect of the invention is a pharmaceutical composition comprising a catalytically active peptide chain or a peptide chain comprising an antibody Fc fragment; and from about 0.125 g to about 1 g of a compound selected from the group consisting of 1-O-n-dodecyl-beta-D-maltopyranoside, 1-O-n-decyl-beta-D-maltopyranoside, 1-O-n-tetradecyl-beta-D-maltopyranoside, and beta-D-fructopyranosyl-alpha-glucopyranoside monododecanoate per 100 ml of the pharmaceutical composition; wherein the diluent is an aqueous buffer at standard state.

Another aspect of the invention is a pharmaceutical composition comprising a catalytically active peptide chain or a peptide chain comprising an antibody Fc fragment; and from about 5 ml to about 20 ml of propylene glycol per 100 ml of the pharmaceutical composition; wherein the diluent is an aqueous buffer at standard state and the propylene glycol is at standard state.

Another aspect of the invention is a pharmaceutical composition comprising a catalytically active peptide chain or a peptide chain comprising an antibody Fc fragment; and about 5 g of heptakis (2,6-di-O-methyl)-beta-cyclodextrin per 100 ml of the pharmaceutical composition; wherein the diluent is an aqueous buffer at standard state.

Another aspect of the invention is a pharmaceutical composition comprising a catalytically active peptide chain or a peptide chain comprising an antibody Fc fragment; and about 2 g of 1,2-didecanoyl-sn-glycero-3-phosphocholine per 100 ml of the pharmaceutical composition; wherein the diluent is an aqueous buffer at standard state and the 1,2-didecanoyl-sn-glycero-3-phosphocholine is emulsified in the aqueous buffer.

Another aspect of the invention is a pharmaceutical composition comprising a catalytically active peptide chain or a peptide chain comprising an antibody Fc fragment; and about 0.1 to about 1 g of a compound selected from the group consisting of sodium glycocholate hydrate, taurocholic acid sodium salt hydrate, and sodium tauroursodeoxycholate per 100 ml of the pharmaceutical composition; wherein the diluent is an aqueous buffer at standard state.

Another aspect of the invention is a pharmaceutical composition comprising a catalytically active peptide chain or a peptide chain comprising an antibody Fc fragment; and from about 1 ml to about 10 ml of tetrahydrofurfuryl polyethyleneglycol per 100 ml of the pharmaceutical composition; wherein the diluent is an aqueous buffer at standard state and the tetrahydrofurfuryl-polyethylenglycol is at standard state.

These and other aspects and embodiments will be apparent from the description, drawings, and sequences herein.

DETAILED DESCRIPTION

Figure 1:
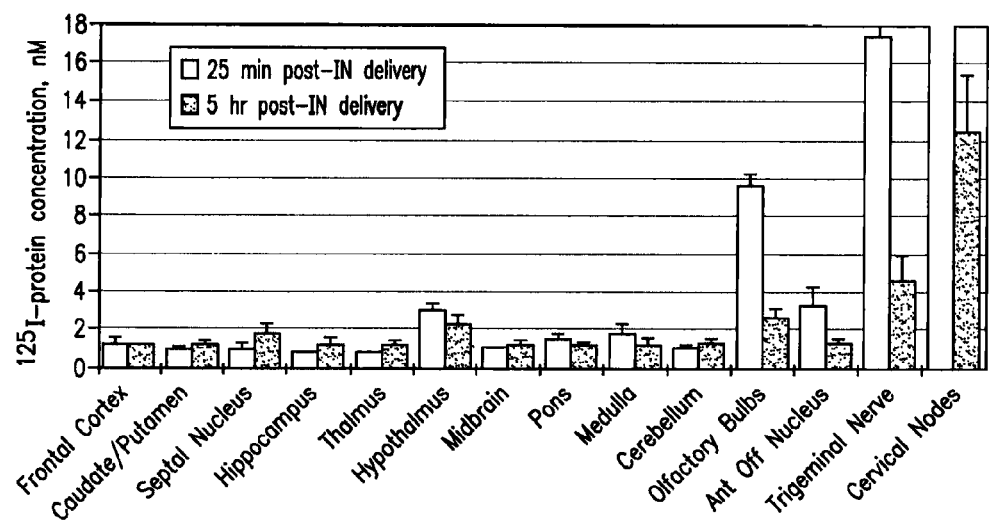
FIG. 1 is a graph showing the distribution of $^{125}$I-α-melanocyte stimulating hormone ($^{125}$I-α-MSH) mimetibody in rats 25 minutes (open bars) and 5 hours (dotted bars) after intranasal administration of $^{125}$I-α-MSH mimetibody, as more fully described in Example 1.

For the purposes of promoting an understanding of the subject matter herein, reference will now be made to preferred embodiments and specific language will be used to describe the same. It will nevertheless be understood that no limitation of the scope of the invention is thereby intended, such alterations and further modifications of the subject matter, and such further applications of the principles as illustrated herein, being contemplated as would normally occur to one skilled in the art to which the subject matter relates.

It has been discovered that globular protein molecules, such as an antibody fragment linked to a therapeutic peptide or protein, can be delivered directly to the central nervous system of a mammal, thereby bypassing the blood-brain barrier. Accordingly, methods of delivering a therapeutic composition to the central nervous system of a mammal are provided. The methods are advantageous in treating a wide variety of diseases or conditions. Methods of treatment are therefore also provided.

Methods of delivering therapeutic compositions to the central nervous system, including the brain and spinal cord and cervical nodes, of a mammal by a non-systemic route, e.g., by a route other than one which delivers or otherwise affects the body as a whole are provided. The delivery method therefore allows for localized and targeted delivery of the therapeutic compositions to the brain via the nasal passage. Consequently, the method relates to delivery of the compositions by a route other than intravenous, intramuscular, transdermal, intraperitoneal, or similar route which delivers the composition through, for example, the blood circulatory system. It has been discovered that antibody fragments conjugated or otherwise linked to a therapeutic polypeptide may be delivered to the central nervous system, including the brain and spinal cord and cervical nodes, of a mammal by administration of the fusion molecule intranasally.

As used herein, the term "polypeptide" intends a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like. In some instances, the terms protein, peptide, and polypeptide are used interchangeably.

The compositions are applied intranasally such that the compositions will be transported to the brain directly, such as by a non-systemic route. Accordingly, methods of delivering therapeutic compositions to the central nervous system of a mammal are provided herein. Methods of treating a disorder responsive to treatment by application of a therapeutic composition to the central nervous system of a mammal are also provided and described below.

A. Composition Components

The therapeutic composition for intranasal delivery is a fusion polypeptide comprised of polypeptide and an antibody or antibody fragment. In one embodiment, the polypeptide is biologically active and preferably causes or otherwise brings about a particular biological effect, such as a therapeutic effect. Various example of polypeptides are given below. The polypeptide is linked to an antibody or antibody fragment directed against an endogenous target. The antibody or antibody fragment, in addition to having binding affinity for a cellular target, may be biologically active to cause a therapeutic effect. Together the polypeptide and the attached antibody or antibody fragment comprise a therapeutic compound or therapeutic fusion polypeptide, that can be formulated as desired for intranasal delivery. As will be illustrated below, the increased size and/or hydrophilicity of the fusion polypeptide, relative to the individual components, reduces the blood bioavailability of the polypeptide while allowing delivery to the central nervous system, thus improving drug targeting while reducing systemic exposure and associated side effects.

i. Antibody or Antibody Fragment

The antibody or antibody fragment in the therapeutic fusion compound may be selected to serve as a targeting agent, to provide a biologically desired effect, or both. The antibody or antibody fragment may be a polyclonal or a monoclonal antibody, and exemplary antibodies and fragments, sources of and preparation of the same, are now described.

Polyclonal antibodies may be obtained by injecting a desired antigen into a subject, typically an animal such as a mouse, as well established in the art. The antigen is selected based on the disorder to be treated. For example, in treating Alzheimer's disease, the antigen may be β-amyloid protein or peptides thereof. In treating cancer, the antigen may be a tumor-associated antigen, such as various peptides known to the art, including, for example, interleukin-13 receptor-α (for malignant astrocytoma/glioblastoma multiforme as discussed in Joshi, B. H. et al., *Cancer Res.* 60:1168-1172 (2000)), BF7/GE2 (microsomal epoxide hydrolase; mEH) (for treatment of tumors with abnormal mEH expression as discussed in Kessler, R. et al., *Cancer Res.* 60:1403-1409 (2000)), tyrosinase-related protein-2 (TRP-2) (for treatment of glioblastoma multiforme), MAGE-1, 3 or 6 (for medulloblastomas) and MAGE-2 (for glioblastoma multiforme) (both as discussed in Scarcella, D. L., et al., *Clin. Cancer Res.*, 5:331-341 (1999)), and survivin (for medulloblastomas as described in Bodey, B. B., *In Vivo,* 18(6)713-718 (2004)). For treatment of neurotrauma to suppress inflammation such as in spinal cord injury and acute brain injury, the antigen may be-TNF-alpha and various interleukins, including interleukin-1. The antigen, along with an adjuvant such as Freund's complete adjuvant, may be injected into the subject multiple times subcutaneously or intraperitoneally.

Another method to increase the immunogenicity of the antigen is to conjugate or otherwise link the antigen to a protein that is immunogenic in the particular species which will produce the antibodies. For example, the antigen may be conjugated to polytuftsin (TKPR40), a synthetic polymer of the natural immunomodulator tuftsin, which has been shown to increase the immunogenicity of synthetic peptides in mice (Gokulan K. et al., *DNA Cell Biol.* 18(8):623-630 (1999)). The method of conjugation may involve use of a bifunctional or derivatizing agent, such as maleimidobenzoyl sulfosuccinimide ester for conjugation through cysteine residues, N-hydroxysuccinimide for conjugation through lysine residues, glutaradehyde or succinic anhydride.

After a sufficient period of time after the initial injection, such as, for example, about one month, the animals may be boosted with a fraction of the original amount of peptide antigen, such as 1/10 the amount, and may then be bled about 7 to 14 days later and the antibodies may be isolated from the blood of the animals by standard methods known to the art, including affinity chromatography using, for example, protein A or protein G sepharose; ion-exchange chromatography, hydroxylapatite chromatography or gel electrophoresis. Antibody purification procedures may be found, for example, in Harlow, D. and Lane E., *Using Antibodies: A Laboratory Manual*, Cold Springs Harbor Laboratory Press, Woodbury, N.Y. (1998); and Subramanian, G., *Antibodies: Production and Purification*, Kluwer Academic/Plenum Publishers, New York, N.Y. (2004).

Non-human antibodies may be humanized by a variety of methods. For example, hypervariable region sequences in the non-human antibodies may be substituted for the corresponding sequences of a human antibody as described, for example, in Jones et al., *Nature*, 321:522-525 (1986); Reichmann et al., *Nature,* 332:323-327 (1988) and Verhoeyen et al., *Science,* 239:1534-1536 (1988). As the antibody is intended for human therapy, it is preferable to select a human variable domain for guidance in making a humanized antibody, in order to reduce the antigenicity of the antibody. In order to accomplish this, the sequence of the variable domain of the non-human antibody may be screened against a library of known human variable domain sequences. The human variable domain sequence which is the closest match to that of the animal is identified and the human framework region within it is utilized in the human antibody as described, for example, in Sims et al., *J. Immunol.,* 151:2296-2308 (1993) and Chothia et al., *J. Mol. Biol.,* 196:901-917 (1987).

The antibody may be a full length antibody or a fragment. The full length antibody or fragment may be modified to allow for improved stability of the antibody or fragment and to modulate effector function, such as binding to an Fc receptor. This may be achieved, for example, by utilizing human or murine isotypes, or variants of such molecules such as IgG4 with Ala/Ala mutations, to lose effector function and yet still maintain IgG structure. The antibody fragment may be a monomer or a dimer, and includes Fab, Fab', F(ab')2, Fc, or an Fv fragment. These fragments may be produced, for example, by proteolytic degradation of the intact antibody. For example, digestion of intact antibodies with papain results in two Fab fragments. Treatment of intact antibodies with pepsin provides a F(ab')2 fragment. The F(ab')2 fragment is a dimer of Fab, which is a light chain joined to VH-CH1 by a disulfide bond. The F(ab)'2 may be reduced under mild conditions to break the disulfide linkage in the hinge region, thereby converting the (Fab')$_2$ dimer into a Fab' monomer. The Fab' monomer is essentially a Fab fragment with part of the hinge region (see Fundamental Immunology, W. E. Paul, ed., Raven Press, N.Y. (1993), for a more detailed description of other antibody fragments).

Many fragments, including those that have the Fc portion, can also be produced by recombinant DNA technology methods known to the art.

A wide variety of antibodies may be used to obtain the antibody fragments utilized in the compositions for intranasal delivery to the central nervous system described herein. Exemplary antibodies include IgG, IgM, IgA, IgD, and IgE. Subclasses of these antibodies may also be used to obtain the antibody fragments. Exemplary subclasses include IgG1, IgG2, IgG3, IgG4, IgA1 and IgA2. The antibody fragments may be obtained by proteolytic degradation of the antibodies which may be produced as previously discussed herein. In one embodiment, the antibody fragment is utilized to increase the half-life of the polypeptide, and antibodies may be isolated from a subject without immunization and may be isolated by antibody isolation procedures previously described herein. Antibody fragments may alternatively be produced by recombinant DNA methods as previously described herein, in order to produce chimeric or fusion polypeptides. For example, a fusion molecule may be produced utilizing a plasmid encoding the respective proteins to generate the mimetibody, which includes the antibody fragment and the therapeutic polypeptide.

Antibodies, antibody fragments or antibody fragments linked to polypeptides, or biologically active portions thereof, may be purified by affinity purification including use of a Protein A column and size exclusion chromatography utilizing, for example, Superose columns. Purification methods are well known in the art. Specific monoclonal antibodies may be prepared by the technique of Kohler and Milstein, *Eur. J. Immunol.*, 6:511-519 (1976) and improvements and modifications thereof. Briefly, such methods include preparation of immortal cell lines capable of producing desired antibodies. The immortal cell lines may be produced by injecting the antigen of choice into an animal, such as a mouse, harvesting B cells from the animal's spleen and fusing the cells with myeloma cells to form a hybridoma. Colonies may be selected and tested by routine procedures in the art for their ability to secrete high affinity antibody to the desired epitope. After the selection procedures, the monoclonal antibodies may be separated from the culture medium or serum by antibody purification procedures known to the art, including those procedures previously described herein.

Alternatively, antibodies may be recombinantly produced from expression libraries by various methods known in the art. For example, cDNA may be produced from ribonucleic acid (RNA) that has been isolated from lymphocytes, preferably from B lymphocytes and preferably from an animal injected with a desired antigen. The cDNA, such as that which encodes various immunoglobulin genes, may be amplified by the polymerase chain reaction (PCR) and cloned into an appropriate vector, such as a phage display vector. Such a vector may be added to a bacterial suspension, preferably one that includes *E. coli*, and bacteriophages or phage particles may be produced that display the corresponding antibody fragment linked to the surface of the phage particle. A sublibrary may be constructed by screening for phage particles that include the desired antibody by methods known to the art, including, for example, affinity purification techniques, such as panning. The sublibrary may then be utilized to isolate the antibodies from a desired cell type, such as bacterial cells, yeast cells or mammalian cells. Methods for producing recombinant antibodies as described herein, and modifications thereof, may be found, for example, in Griffiths, W. G. et al., *Ann. Rev. Immunol.*, 12:433-455 (1994); Marks, J. D. et al., *J. Mol. Biol.*, 222:581-597 (1991); Winter, G. and Milstein, C., *Nature*, 349:293-299 (1991); and Hoogenboom, H. R. and Winter, G., *J. Mol. Biol.*, 227(2):381-388 (1992).

Human antibodies may also be produced in transgenic animals. For example, homozygous deletion of the antibody heavy chain joining region ($J_H$) gene in chimeric and germ-line mutant mice results in complete inhibition of endogenous antibody production such that transfer of a human germ-line immunoglobulin gene array into such mutant mice results in production of human antibodies when immunized with antigen. See, e.g., Jakobovits et al., *Proc. Natl. Acad. Sci. USA*, 90:2551-2551 (1993); Jakobovits et al., *Nature*, 362:255-258 (1993); U.S. Pat. Nos. 5,545,806; 5,569,825; 5,591,669; 5,545,807 and PCT publication WO 97/17852.

ii. Polypeptide

As noted above, the antibody or antibody fragment is linked to a polypeptide. Preferably, the polypeptide is one that may bind to a region of the central nervous system. The polypeptide is further preferably one that has a beneficial effect on the central nervous system, and includes one that has a beneficial effect on functions regulated by the central nervous system of a mammal, such as for therapeutic purposes.

The polypeptide may exert its effects by binding to, for example, cellular receptors in various regions of the brain. As one example, in order for α-melanocyte stimulating hormone (α-MSH) to exert its effect in body weight reduction, it binds to the melanocortin 4 receptor (MCR-4) on neurons in the hypothalamus. As a further example, in order for erythropoietin (EPO), active EPO fragments or EPO analogs to improve neurologic function after stroke or acute brain injury, it has to bind to neuronal receptors, e.g., on hippocampal cells, astrocytes, or similar cells.

A wide variety of proteins or peptides may be utilized. The polypeptides may have a molecular weight of about 200 Daltons to about 200,000 Daltons, but are typically about 300 Daltons to about 100,000 Daltons.

In one embodiment, the polypeptide and antibody or antibody fragment, after attachment, have a combined molecular weight of greater than about 25 kDa, more preferably of greater than about 30 kDa, still more preferably of greater than about 40 kDa.

In another embodiment, the polypeptide has a molecular weight of less than about 25 kDa and is hydrophobic.

A wide variety of therapeutic proteins, or biologically active portions thereof, may be linked or otherwise attached to the antibody fragments that may be utilized in the methods described herein. The proteins are preferably in the form of peptides. The specific therapeutic peptide selected will depend on the disease or condition (collectively referred to as "disorder") to be treated. For neurodegenerative disorders, such as, for example, Alzheimer's disease, Parkinson's disease and Huntington's disease, or other disease involving loss of locomotion or cognitive function such as memory, neuroprotective or neurotrophic agents are preferred. The neuroprotective or neurotrophic agent may be one that promotes neuronal survival, stimulates neurogenesis and/or synaptogenesis, rescues hippocampal neurons from beta-amyloid-induced neurotoxicity and/or reduces tau phosphorylation. Examples of agents suitable for treating such neurodegenerative disorders, and neurological disorders, include leutenizing hormone releasing (LHRH) and agonists of LHRH, such as deslorelin; neurotrophic factors, such as those from the neurotrophin family, including nerve growth factor (NGF), brain-derived neurotrophic factor (BDNF), neurotrophin-3 and neurotrophin-4/5; the fibroblast growth factor family (FGFs), including acidic fibroblast growth factor and basic fibroblast growth factor; the neurokine family, including ciliary neurotrophic factor, leukemia inhibitory factor, and cardiotrophin-1; the transforming growth factor-β family, including transforming growth factor-β-1-3 (TGF-betas), bone morphogenetic proteins (BMPs), growth/differentiation factors such as growth differentiation factors 5 to 15, glial cell line-derived neurotrophic factor (GDNF), neurturin, artemin, activins and persephin; the epidermal growth factor family, including epidermal growth factor, transforming growth factor-α and neuregulins; the insulin-like growth factor family, including insulin-like growth factor-1 (IGF-1) and insulin-like growth factor-2 (IGF-2); the pituitary adenylate cyclase-activating polypeptide (PACAP)/glucagons superfamily, including PACAP-27, PACAP-38, glucagons, glucagons-like peptides such as GLP-1 and GLP-2, growth hormone releasing factor, vasoactive intestinal peptide (VIP), peptide histidine methionine, secreting and glucose-dependent insulinotropic polypeptide; and other neurotrophic factors, including activity-dependent neurotrophic factor and platelet-derived growth factors (PDGFs). Such agents are also suitable for treating acute brain injury, chronic brain injury (neurogenesis) and neuropsychologic disorders, such as depression.

In the case of stroke treatment, the therapeutic agent may be one that protects cortical neurons from nitric oxide-mediated neurotoxicity, promotes neuronal survival, stimulates neurogenesis and/or synaptogenesis and/or rescues neurons from glucose deprivation. Examples of such agents include the neurotrophic factors previously described herein, active fragments thereof, as well as erythropoietin (EPO), analogs of EPO, such as carbamoylated EPO, and active fragments of EPO. Examples of EPO analogs that may be used include those known to the skilled artisan and described, for example, in U.S. Pat. Nos. 5,955,422 and 5,856,298. Peptide growth factor mimetics of, and antagonists to, for example, EPO, granulocyte colony-stimulating factor (GCSF), and thrombopoietin useful in the invention can be screened for as reviewed by K. Kaushansky, *Ann. NY Acad. Sci.,* 938:131-138 (2001) and as described for EPO mimetic peptide ligands by Wrighton et al., *Science,* 273(5274):458-450 (1996). The mimetics, agonists and antagonists to the peptide growth factors, or other peptides or proteins described herein, may be shorter in length than the peptide growth factor or other polypeptide that the mimetic, agonist or antagonist is based on.

Therapeutic polypeptides for treatment of eating disorders, such as for prevention of weight loss (anorexia) and weight gain (obesity), include melanocortin receptor (MCR) agonists and antagonists. Suitable MCR agonists include α-melanocyte stimulating hormone (α-MSH) as well as beta and gamma-MSH, and derivatives thereof, including amino acids 1 to 13 of human α-MSH (SEQ ID NO:1 SYSMEHFR-WGKPV) and specifically receptor binding amino acid sequence 4-10, as in adrenocorticotropic hormone (MSH/ACTH$_{4-10}$), melanocortin receptor-3 (MCR3) or melanocortin receptor 4 (MCR4) agonists, such as melanotan II (MTII), a potent non-selective MCR agonist, MRLOB-0001 and active fragments of the peptides and/or proteins. Other peptides for obesity treatment include hormone peptide YY (PYY), especially amino acids 3 to 36 of the peptide, leptin and ghrelin, ciliary neurotrophic factor or analogs thereof, glucagon-like peptide-1 (GLP-1), insulin mimetics and/or sensitizers, leptin, leptin analogs and/or sensitizers and dopaminergic, noradrenergic and serotinergic agents.

Corresponding MCR antagonists regulating body weight homeostasis include endocannabinoid receptor antagonists, fatty acid synthesis receptor inhibitors, ghrelin antagonists, melanin-concentrating hormone receptor antagonists, PYY receptor antagonists and tyrosine phosphatase-1B inhibitors (J. Korner et al., *J. Clin. Invest.,* 111:565-570 (2003)). MCR antagonists, such as Agouti signaling protein (ASIP) and Agouti-related protein (AGRP), which are endogenous MCR3 and MCR4 antagonists, and their peptoid variants and mimetics may be used to control body weight homeostasis and to treat eating disorders such as anorexia (YK Yang et al., *Neuropeptides,* 37(6):338-344 (2003); DA Thompson et al, *Bioorg Med Chem. Lett.,* 13:1409-1413 (2003); and C. Chen et al, *J. Med. Chem.,* 47(27):6821-30 (2004)).

The previously mentioned peptide hormones and analogs thereof that bind to melanocortin receptors (MCRs) may also be useful to control inflammation and improve male and female sexual dysfunction (A. Catania et al., *Pharmacol Rev,* 56(1): 1-29 (2004)).

The therapeutic protein for treatment of endocrine disorders, such as diabetes mellitus includes, for example, glucagon-like peptide 1 (GLP-1); peptides from the GLP-1 family, including pituitary adenylate cyclase-activating polypeptide (PACAP), vasoactive intestinal peptide (VIP), exendin-3 and exendin-4; and insulin-like growth factor (IGF-1), IGF binding protein 3 (IGFBP3) and insulin, and active fragments thereof.

The therapeutic polypeptide for treatment of sleep disorders, such as insomnia, includes growth hormone releasing factor, vasopressin, and derivatives of vasopressin, including desmopressin, glypressin, ornipressin and ternipressin; Included are peptide variants and mimetic peptide ligands that bind to the same receptor targets resulting in either the same/similar or the opposite biological response. The therapeutic protein for treatment of autoimmune disorders, such as multiple sclerosis, includes interferons, including β-interferon, and transforming growth factor β's.

The therapeutic polypeptide for treatment of psychiatric disorders, such as schizophrenia, includes neuregulin-1, EPO, analogs of EPO, such as carbamoylated EPO, and active fragments of EPO and EPO mimetics as previously described herein. Various neurotrophic factors and regulatory peptide hormones, such as brain-derived neurotrophic factor (BDGF) and insulin, may be used to treat depression, and psychoendocrinologic and metabolic disorders.

The therapeutic polypeptide for treatment of lysosomal storage disorders of the brain includes, for example, lysosomal enzymes.

The therapeutic polypeptide for treatment of eating disorders such as anorexia includes, for example, melanocortin receptor (MCR) antagonists such as Agouti signaling protein (ASIP) and Agouti related protein (AGRP).

The therapeutic polypeptides may be human polypeptides, although the polypeptides may be from other species or may be synthetically or recombinantly produced. The original amino acid sequence may also be modified or reengineered such as for improved potency or improved specificity (e.g. eliminate binding to multiple receptors) and stability.

Therapeutic polypeptides utilized herein may also be mimetics, such as molecules that bind to the same receptor but have amino acid sequences that are non-homologous to endogenous human peptides. For example, the agonist and antagonists, including agonists and antagonists of melanocortin receptor, growth hormone releasing factor receptor, vasopressin receptor, hormone peptide YY receptor, a neuropeptide Y receptor, or erythropoietin receptor, may include natural amino acids, such as the L-amino acids or non-natural amino acids, such as D-amino acids. The amino acids in the polypeptide may be linked by peptide bonds or, in modified peptides, including peptidomimetics, by non-peptide bonds (J. Zhang et al., *Org. Lett.,* 5(17): 3115-8 (2003)).

Polypeptide mimetics, and receptor agonists and antagonists can be selected and produced utilizing high throughput screening known to the art for specific biological function and receptor binding. The availability of such methods allows rapid screening of millions of randomly produced organic compounds and peptides to identify lead compounds for further development. Strategies used to screen libraries of small molecules and peptides and the success in finding mimetics and antagonists, e.g., for/to EPO, GCSF and thrombopoietin, are reviewed by K. Kaushansky, *Ann. NY Acad. Sci.,* 938:131-138 (2001).

A wide variety of modifications to the amide bonds which link amino acids may be made to the agonists and antagonists described herein, and such modifications are well known in the art. For example, such modifications are discussed in general reviews, including in Freidinger, R. M. "Design and Synthesis of Novel Bioactive Peptides and Peptidomimetics" *J. Med. Chem.,* 46:5553 (2003), and Ripka, A. S., Rich, D. H. "Peptidomimetic Design" *Curr. Opin. Chem. Biol.,* 2:441

(1998). Many of the modifications are designed to increase the potency of the peptide by restricting conformational flexibility.

For example, the agonists and antagonists may be modified by including additional alkyl groups on the nitrogen or alpha-carbon of the amide bond, such as the peptoid strategy of Zuckerman et al, and the alpha modifications of, for example Goodman, M. et. al. (*Pure Appl. Chem.*, 68:1303 (1996)). The amide nitrogen and alpha carbon may be linked together to provide additional constraint (Scott et al, *Org. Letts.*, 6:1629-1632 (2004)).

iii. Linkages

The polypeptide is linked to the antibody or antibody fragment to form the therapeutic compound for delivery. The antibody or antibody fragment, in one embodiment, increases the stability of the polypeptide, thereby increasing its half life in vivo, including in the nasal cavity and the central nervous system of a mammal. The combined polypeptide-antibody fragment compound is also referred to herein as a "mimetibody". In this section, approaches for linking the two moieties is described.

The antibody fragment and polypeptide may be linked to each other by methods known to the art, and typically through covalent bonding. The linking or conjugation method may include use of amino acid linkers, including use of glycine and serine. The fragment and polypeptide may be conjugated or otherwise linked by cross-linking or other linking procedures know to the art and discussed, for example, in Wong, S. S., *Chemistry of Protein Conjugation and Cross-Linking*, CRC Press, Boca Raton, Fla. (1991). For example, the polypeptides may be conjugated utilizing homo-bifunctional and/or hetero-bifunctional or multifunctional cross-linkers known to the art. Examples of cross-linking agents include carbodiimides, such as EDC (1-Ethyl-3-[3-dimethylaminopropyl]carbodiimide hydrochloride); imidoesters, N-hyroxysuccinimide-esters, maleimides, pyridyl disulfides, hydrazides and aryl azides. Several points of attachment between the active agent polypeptide and the antibody fragment are envisioned, including linkage of the N-terminus of the peptide to the C-terminus of the antibody fragment. The polypeptide may, alternatively, be attached at its C-terminus to the N-terminus of the antibody fragment. Conjugation may further be via cysteine or other amino acid residues or via a carbohydrate functional moiety of the antibody.

iv. Formulation of the Therapeutic Polypeptide-Antibody Compound

The active agent polypeptide in the therapeutic composition may be mixed with a pharmaceutically-acceptable carrier or other vehicle. The carrier may be a liquid suitable, for example, for administration as nose drops or as a nose spray, and includes water, saline or other aqueous or organic and preferably sterile solution. The carrier may be a solid, such as a powder, gel or ointment and may include inorganic fillers such as kaolin, bentonite, zinc oxide, and titanium oxide; viscosity modifiers, antioxidants, pH adjusting agents, lyoprotectants and other stability enhancing excipients, including sucrose, antioxidants, chelating agents; humectants such as glycerol, and propylene glycol; and other additives which may be incorporated as necessary and/or desired.

Where the therapeutic compound is administered as a gel or ointment, the carrier may include suitable solid, such as a pharmaceutically acceptable base material known for use in such carriers, including, for example, natural or synthetic polymers such as hyaluronic acid, sodium alginate, gelatin, corn starch, gum tragacanth, methylcellulose, hydroxyethylcellulose, carboxymethylcellulose, xanthan gum, dextrin, carboxymethylstarch, polyvinyl alcohol, sodium polyacrylate, methoxyethylene maleic anhydride copolymer, polyvinylether, polyvinylpyrrolidone; fats and oils such as beeswax, olive oil, cacao butter, sesame oil, soybean oil, camellia oil, peanut oil, beef fat, lard, and lanolin; white petrolatum; paraffins; hydrocarbon gel ointments; fatty acids such as stearic acid; alcohols such as cetyl alcohol and stearyl alcohol; polyethylene glycol; and water.

Where the therapeutic compound is administered as a powder, the carrier may be a suitable solid such as oxyethylene maleic anhydride copolymer, polyvinylether, polyvinylpyrrolidone polyvinyl alcohol; polyacrylates, including sodium, potassium or ammonium polyacrylate; polylactic acid, polyglycolic acid, polyvinyl alcohol, polyvinyl acetate, carboxyvinyl polymer, polyvinylpyrrolidone, polyethylene glycol; celluloses, including cellulose, microcrystalline cellulose, and .alpha.-cellulose; cellulose derivatives, including methyl cellulose, ethyl cellulose, hydroxyethyl cellulose, hydroxypropyl cellulose, hydroxypropyl methyl cellulose, sodium carboxymethyl cellulose and ethylhydroxy ethyl cellulose; dextrins, including alpha-, .beta- or .gamma-cyclodextrin, dimethyl-beta.-cyclodextrin; starches, including hydroxyethyl starch, hydroxypropyl starch, carboxymethyl starch; polysaccharides, including dextran, dextrin and alginic acid; hyaluronic acid; pectic acid; carbohydrates, such as mannitol, glucose, lactose, fructose, sucrose, and amylose; proteins, including casein, gelatin, chitin and chitosan; gums, such as gum arabic, xanthan gum, tragacanth gum and glucomannan; phospholipids and combinations thereof.

The particle size of the powder may be determined by standard methods in the art, including screening or sieving through appropriately sized mesh. If the particle size is too large, the size can be adjusted by standard methods, including chopping, cutting, crushing, grinding, milling, and micronization. The particle size of the powders typically range from about 0.05 μm to about 100 μm. The particles are preferably no larger than about 400 μm.

The compositions may further include agents which improve the mucoadhesivity, nasal tolerance, or the flow properties of the composition, mucoadhesives, absorption enhancers, odorants, humectants, and preservatives. Suitable agents which increase the flow properties of the composition when in an aqueous carrier include, for example, sodium carboxymethyl cellulose, hyaluronic acid, gelatin, algin, carageenans, carbomers, galactomannans, polyethylene glycols, polyvinyl alcohol, polyvinylpyrrolidone, sodium carboxymethyl dextran and xantham gum. Suitable absorption enhancers include bile salts, phospholipids, sodium glycyrrhetinate, sodium caprate, ammonium tartrate, gamma.aminolevulinic acid, oxalic acid, malonic acid, succinic acid, maleic acid and oxaloacetic acid. Suitable humectants for aqueous compositions include, for example, glycerin, polysaccharides and polyethylene glycols. Suitable mucoadhesives include, for example, polyvinyl pyrrolidone polymer.

Another aspect of the invention is pharmaceutical compositions that may further include permeation enhancer agents that enhance delivery of protein substances to the central nervous system via intranasal administration. The protein substances can be whole antibodies, antibody fragments known to those skilled in the art such as Fab fragments or Fc-containing protein substances such as mimetibodies. Further, the protein substance can be a catalytically active protein such as an enzyme. The protein substances administered are useful for prophylactic, therapeutic or diagnostic purposes.

Absorption enhancers facilitate the transport of molecules through the mucosa, which includes the mucous, and the epithelial cell membrane. A variety of absorption enhancer classes have been described, including mucoadhesives, ciliary beat inhibitors, mucous fluidizers, membrane fluidizers, and tight junction modulators. In the present invention, membrane fluidizers and tight junction modulators most effectively increase the delivery of protein substances, deposited on the nasal epithelium, to the CNS.

Tight junctions are intercellular structures that restrict paracellular transport between the apical and basolateral sides of an epithelial layer or between aspects of certain specialized cells including neurons, activated immune cells, and some endothelial cells. The permeability of the tight junctions varies between tissues in the body; tight junctions generally limit transport to those molecules with a hydrodynamic radius less than 3.6 A and disallow significant transport of molecules with a radius larger than 15 A (Stevenson, B. R. et al., Mol. Cell Biochem 83:129-145 (1988)). See also Illum L, *J. Pharm. Pharmacol,* 56:3-17 (2004).

Tight junctions are composed of integrated transmembrane and intracellular proteins and the adjacent membranous microdomains. Tight junction permeability is modulated by intra- and extra-cellular stimuli that modify tight junction proteins or lipids thereby changing their physical interactions with each other and leading to either more restricted or less restricted paracellular transport. Some chemicals have been shown to mimic these intra- and extra-cellular stimuli to induce temporary changes in either the proteins or lipids in the tight junctions to result in reversible increases in paracellular transport. Including these chemicals as excipients in formulations allows increased amounts of a molecule to pass through the nasal epithelium or between the axons and adjacent cells to enter paracellular and perineurial spaces (extracellular spaces).

The functionality of such membrane modifiers can be measured by their barrier disruption potential (reduction in TEER) and visualized by microscopic methods (e.g., fluorescence light microscope, electron microscope). The functionalities include extraction or fluidization of lipid bilayers or disruption of cell membrane protein interactions, e.g., via perturbation, disruption of intermolecular ionic forces such as hydrogen bonding or specific binding. This can be achieved via solvents such as propylene glycol, glycofurol and glycerol or bile salts and ionic or nonionic surfactants such as glycocholate, taurocholate and tauroursodeoxycholate and alkylglycosides such as decyl, dodecyl and tetradecyl maltosides or lipids such as lysophopsphatidylcholine (LPC), 1,2-didecanoyl-sn-glycero-3-phosphocholine (DDPC) and fatty acids such as oleic acid or charged compounds such as chitosan and others as typically described in the art.

The enhancers as described in Example 7 and listed in Table A herein are representative examples of membrane modifiers and include chitosan glutamate, n-dodecyl-beta-D-maltopyranoside, n-decyl-beta-D-maltopyranoside, n-tetradecyl-beta-D-maltopyranoside, beta-D-fructopyranosyl-alpha-glucopyranoside monododecanoate, propylene glycol, heptakis(2,6-di-O-methyl)-beta-cyclodextrin, 1,2-didecanoyl-sn-glycero-3-phosphocholine, sodium glycocholate hydrate, taurocholic acid sodium salt hydrate, sodium tauroursodeoxycholate, and tetrahydrofurfuryl polyethyleneglycol. Naming conventions, sources and other relevant information for these compounds is provided in Table A.

TABLE A

| Shorthand Designation or Name for Compound | Compound Name(s) | Source of Compound Preparation | Purity by Mass of Compound in Compound Preparation & Other Characteristics of the Compound Preparation |
|---|---|---|---|
| chitosan | chitosan glutamate | NovaMatrix USA d.b.a. FMC BioPolymer AS (Sandvika, Norway) | A chitosan preparation in which 75-90% of the acetyl groups are deacetylated. Typically, the molecular weight for chitosan glutamate in the PROTASAN UP G 213 is in the 20,0000 to 60,0000 g/mol range (measured as a chitosan acetate). |
| Intravail A3 | n-dodecyl-beta-D-maltopyranoside; dodecyl maltoside (C12 chain length) | Inalco SpA (Milano, Italy) | ≥99% |
| Intravail A5 | n-tetradecyl-beta-D-maltopyranoside; tetradecyl maltoside; (C14 chain length) TDM | Inalco SpA (Milano, Italy) | ≥99% |
| Intravail B3 | beta-D-fructopyranosyl-alpha-glucopyranoside monododecanoate; sucrose monododecanoate; dodecanoyl sucrose; lauroyl sucrose | Anatrace, Inc. (Maumee, OH) | 98.90% |
| Intravail A1 | n-decyl-beta-D-maltopyranoside (C10 chain length) | Aegis Therapeutics, LLC (San Diego, CA) | N/A |
| propylene glycol | propylene glycol | Dow Chemical (Midland, MI) | 99.50% |
| di-methyl-beta-cyclodextrin | heptakis(2,6-di-O-methyl)-beta-cyclodextrin | Sigma (St. Louis, MO) | N/A |
| DDPC | 1,2-didecanoyl-sn-glycero-3-phosphocholine | Sigma (St. Louis, MO) | 99% |

TABLE A-continued

| Shorthand Designation or Name for Compound | Compound Name(s) | Source of Compound Preparation | Purity by Mass of Compound in Compound Preparation & Other Characteristics of the Compound Preparation |
|---|---|---|---|
| sodium glycocholate | sodium glycocholate hydrate | Sigma (St. Louis, MO) | >97% |
| sodium taurocholate | taurocholic acid sodium salt hydrate | Aldrich (St. Louis, MO) | 97% |
| tauroursodeoxycholate | sodium tauroursodeoxycholate | Sigma (St. Louis, MO) | 90% |
| glycofurol | Tetrahydrofurfuryl-polyethylenglycol ether | Alchymars (Milano, Italy) | N/A |

The term "peptide chain" means a molecule comprising at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "catalytically active" means a molecule that is capable of increasing the rate of a chemical reaction. Such chemical reactions may include synthetic, decomposition, combustion, single displacement, double displacement, acid-base equilibrium, reduction-oxidation, or other physical processes such as particle release (e.g. ion release) or other changes that are thermodynamically favorable. Examples of "catalytically active" peptide chains include enzymes, such as beta-lactamases or lysosomal enzymes, and allosteric effectors. Those skilled in the art will recognize other such catalytically active peptide chains.

Figure 11:
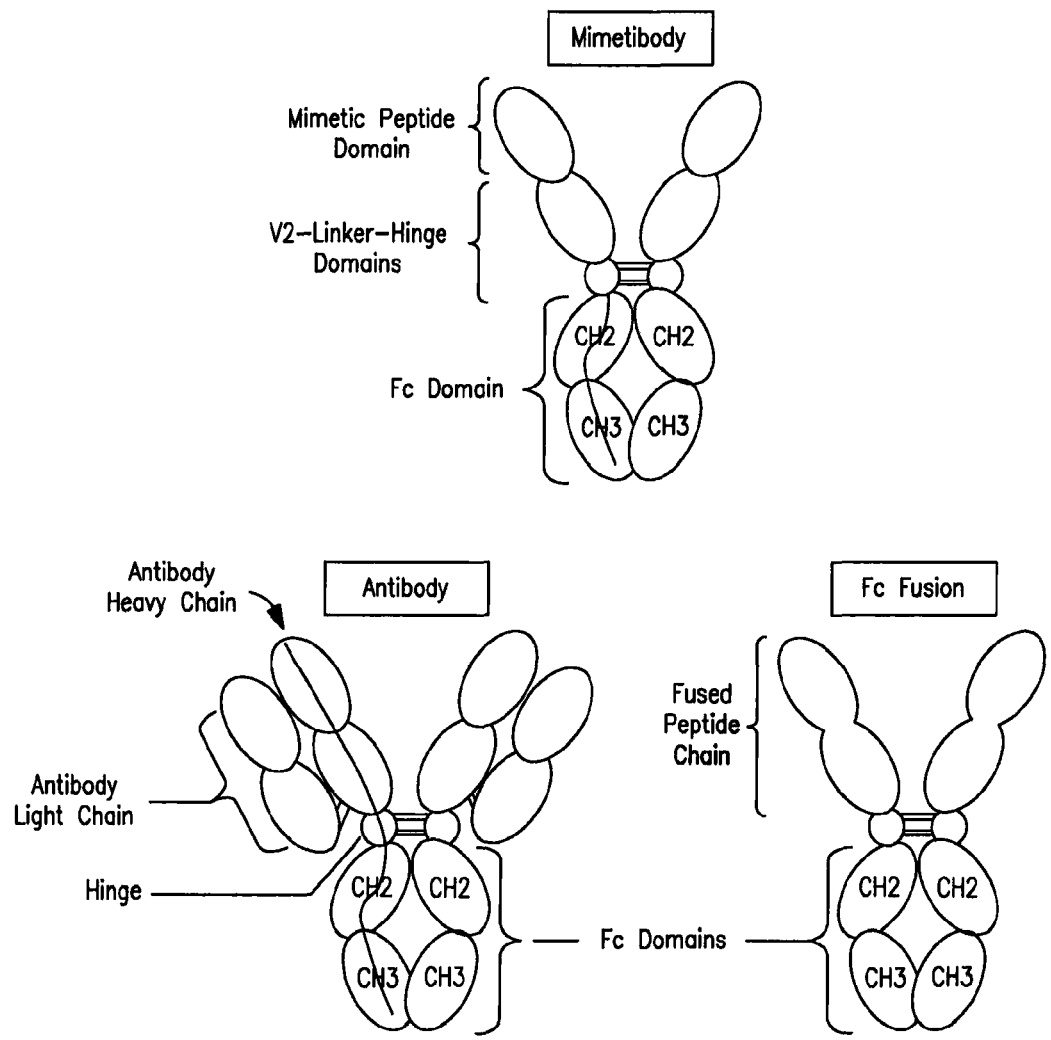
FIG. 11 is a schematic of representative peptide chains comprising antibody Fc fragments. Selected peptide chain features are noted.

The term "antibody Fc fragment" means a peptide chain comprising a portion of an immunoglobulin heavy chain $C_H2$ constant region peptide chain and immunoglobulin heavy chain $C_H3$ constant region peptide chains sufficient to bind protein A. Such constant region peptide chains may be derived from antibody heavy chains of any isotype, such as $IgG_1$, and may also be referred to as an "Fc domain" (see e.g. FIG. 11) or "Fc peptide chain." An antibody Fc fragment may be an individual peptide chain comprising both an immunoglobulin heavy chain $C_H2$ constant region peptide chain and an immunoglobulin heavy chain $C_H3$ constant region peptide chain sufficient to bind protein A (e.g. single chain antibody) or an association of two such individual peptide chains (e.g. antibody or mimetibody). "Peptide chains comprising an antibody Fc fragment" represent a genus of molecules that includes, for example, antibody molecules comprising Fc domains, Fc fusion peptide chains comprising Fc domains, and mimetibody peptide chains comprising Fc domains (FIG. 11). The term "antibody Fc fragment" can be used to describe unaggregated Fc peptide chains, aggregated Fc peptide chains, or both aggregated and unaggregated Fc peptide chains.

The term "emulsion" means a mixture of at least two immiscible substances such that one substance (the dispersed phase) is dispersed in the other (the continuous phase). A compound is said to be "emulsified" when it is present in an emulsion, typically in the dispersed phase.

The invention provides liquid pharmaceutical compositions comprising various formulations useful and acceptable for nasal administration to an animal or human patient. Such pharmaceutical compositions are prepared using aqueous buffers at "standard state" as the diluent, and in some aspects of the invention liquid compounds such as propylene glycol or tetrahydrofurfuryl-polyethylenglycol ether at standard state. The liquid pharmaceutical compositions of the invention can be prepared using routine methods well known to those of ordinary skill in the art. For example, the aqueous buffer component of the pharmaceutical composition may be provided first followed by the addition of an appropriate mass or volume of the other components of the pharmaceutical composition at "standard state." The desired amount of a catalytically active peptide chain or a peptide chain comprising an antibody Fc or Fab fragment may then be added. Last, the volume of the pharmaceutical composition is adjusted to the desired final volume under "standard state" conditions using aqueous buffer as the diluent. Those skilled in the art will recognize a number of other methods suitable for the preparation of the claimed pharmaceutical compositions and would also recognize that the pharmaceutical compositions of the invention could be prepared in powder or lyophilized form.

Aqueous buffers suitable for use in the pharmaceutical compositions and methods of the invention are physiologically acceptable for nasal administration. The pH of such buffers must be physiologically acceptable for nasal administration and compatible with the nasal delivery of a catalytically active peptide chain or a peptide chain comprising an antibody Fc or Fab fragment to the central nervous system. The pH of such an aqueous buffer may be between pH 4.0 and pH 8.0 with a pH of about 6.0 to 7.6 being preferred. Phosphate, acetate, borate, phthalate and amino acid based aqueous buffers such as histidine based buffers are examples of physiologically acceptable buffers. Phosphate buffered saline (PBS) with a pH of 7.4 at "standard state" is one example of an aqueous buffer suitable for use in the pharmaceutical compositions of the invention and is a preferred aqueous buffer. PBS comprises 0.138 M NaCl, 0.0027 M KCl with a pH of 7.4 "standard state." Those skilled in the art will recognize other aqueous buffers suitable for the preparation of the claimed pharmaceutical compositions and for use in the methods of the invention.

The claimed pharmaceutical compositions may be aqueous solutions or suspensions, such as emulsions, comprising the indicated mass, or volume, of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere). Additionally, the pharmaceutical compositions of the invention are described in terms of the mass, or volume at standard state, of a given component per a 100 ml volume of the pharmaceutical composition. As those in the art will recognize, this is simply one way of facilitating a description of the pharmaceutical compositions of the invention and should not be construed as limiting the claims (e.g. to a 100 ml volume of the pharmaceutical composition).

Importantly, the pharmaceutical compositions of the invention may contain component masses "about" a certain value (e.g. "about 1 g of sodium tauroursodeoxycholate") per unit volume of the pharmaceutical composition or have pH values about a certain value. A component mass or volume present in a pharmaceutical composition or pH value is "about" a given numerical value if the catalytically active peptide chain or peptide chain comprising an antibody Fc or Fab fragment present in the pharmaceutical composition is biologically active while such peptide chains are present in the pharmaceutical composition or after such peptide chains have been removed from the pharmaceutical composition (e.g. by dilution or delivery). Stated differently, a value, such as a component mass value, volume value or pH value, is "about" a given numerical value when the catalytic activity of a catalytically active peptide chain or the binding activity of the peptide chain comprising an antibody Fc or Fab fragment is maintained and detectable after placing the isolated antibody in the pharmaceutical composition.

Alternatively, a value, such as a component mass value, volume value or pH value, is "about" a given numerical value when the value is within a range that includes values that are uncorrected for the purity by, mass or volume, of the component compound in a given compound preparation and values that have been corrected for the purity, by mass or volume, of a component compound in a given compound preparation. For example, if a given compound preparation is 90% pure by mass for a given component compound values "about" 1 g would include 0.9 g, 1 g, and 1.1 g since these values are in the range described above. This reflects the practical fact that for many compound preparations the actual purity by mass or volume of a given compound in the preparation is not known with absolute certainty, but is instead only know within the limits of the assay techniques used. Furthermore, due to the heterogenous nature of some compounds such as polymers and hydrates it is often difficult to describe the purity of the compound by mass because the mass of the compounds in the preparation, such as polymers, or the mass and stoichiometry of hydrate in the preparation is variable or undetermined.

Last, a value such as the molecular mass in Dalton based units is "about" a given numerical value when the value is within a range that includes the standard deviation observed when using a technique, such a SDS-PAGE, for measuring the molecular mass of a peptide chain. For example, if the mean molecular mass in Daltons of a peptide chain as measure by SDS-PAGE is 25,000 Daltons with a standard deviation of (+/−) 5,000 Daltons then values "about" 25,000 Daltons are those in the range 20,000 Daltons; 25,000 Daltons; and 30,000 Daltons.

One aspect of the invention is a pharmaceutical composition comprising a catalytically active peptide chain or a peptide chain comprising an antibody Fc or Fab fragment; and about 0.1 to about 1.0 g, such as 0.5 g, of chitosan glutamate or corresponding amounts of another chitsoan salt per 100 ml of the pharmaceutical composition; wherein the diluent is an aqueous buffer at standard state. Chitosan salts, such as chitosan glutamate, useful in the pharmaceutical compositions and methods of the invention includes chitosans with different molecular weights including for example chitosans with molecular weights of 50,000 g/mol to 60,000 g/mol and which are approximately 90% deacetylated. Other chitosan salts such as, for example, chitosan chloride and others recognized by those of ordinary skill in the art may also be used in the compositions and methods of the invention.

Another aspect of the invention is a pharmaceutical composition comprising a catalytically active peptide chain or a peptide chain comprising an antibody Fc or Fab fragment; and from about 0.125 g to about 1 g, such as about 0.5 g or less, of a compound selected from the group consisting of n-dodecyl-beta-D-maltopyranoside, n-decyl-beta-D-maltopyranoside, n-tetradecyl-beta-D-maltopyranoside, and beta-D-fructopyranosyl-alpha-glucopyranoside monododecanoate per 100 ml of the pharmaceutical composition; wherein the diluent is an aqueous buffer at standard state.

Another aspect of the invention is a pharmaceutical composition comprising a catalytically active peptide chain or a peptide chain comprising an antibody Fc or Fab fragment; and from about 5 ml to about 20 ml, such as about 10 ml to about 20 ml, of propylene glycol per 100 ml of the pharmaceutical composition; wherein the diluent is an aqueous buffer at standard state and the propylene glycol is at standard state.

Another aspect of the invention is a pharmaceutical composition comprising a catalytically active peptide chain or a peptide chain comprising an antibody Fc fragment; and about 1 g to about 10 g, such as about 5 g, of heptakis (2,6-di-O-methyl)-beta-cyclodextrin per 100 ml of the pharmaceutical composition; wherein the diluent is an aqueous buffer at standard state.

Another aspect of the invention is a pharmaceutical composition comprising a catalytically active peptide chain or a peptide chain comprising an antibody Fc fragment; and about 1 g to about 5 g, such as about 2 g, of 1,2-didecanoyl-sn-glycero-3-phosphocholine per 100 ml of the pharmaceutical composition; wherein the diluent is an aqueous buffer at standard state and the 1,2-didecanoyl-sn-glycero-3-phosphocholine is emulsified in the aqueous buffer. Methods for emulsification such as sonication, the use of stabilizing surfactants and the like are well known in the art and are suitable for preparing the pharmaceutical compositions of the invention comprising 1,2-didecanoyl-sn-glycero-3-phosphocholine in emulsion.

Another aspect of the invention is a pharmaceutical composition comprising a catalytically active peptide chain or a peptide chain comprising an antibody Fc fragment; and about 01 g to about 1 g, such as about 1 g, of a compound selected from the group consisting of sodium glycocholate hydrate, taurocholic acid sodium salt hydrate, and sodium tauroursodeoxycholate per 100 ml of the pharmaceutical composition; wherein the diluent is an aqueous buffer at standard state. Other salts of these compounds which will be readily recognized by those of ordinary skill in the art may also be used in the compositions and methods of the invention.

Another aspect of the invention is a pharmaceutical composition comprising a catalytically active peptide chain or a peptide chain comprising an antibody Fc or Fab fragment; and from about 1 ml to about 10 ml of tetrahydrofurfuryl-polyethylenglycol per 100 ml of the pharmaceutical composition; wherein the diluent is an aqueous buffer at standard state and the tetrahydrofurfuryl-polyethyleneglycol is at standard state.

In another embodiment of the pharmaceutical composition of the invention, the peptide chain comprises an antibody Fc fragment that binds to a melanocortin 4 receptor comprising the amino acid sequence shown in SEQ ID NO: 2. Such binding can be assayed by a variety of well known techniques such as, for example, ELISAs, Western blots, BIACORE™ (GE Healthcare, Piscataway, N.J.) instrumentation based techniques and the like.

In another embodiment of the pharmaceutical compositions of the invention, the peptide chain comprising an antibody Fc fragment comprises the amino acid sequence shown in SEQ ID NO: 3.

In one embodiment of this pharmaceutical composition the aqueous buffer is phosphate buffered saline (PBS) at about pH 7.4.

B. Nasal Delivery

The term "nasal cavity" means the large air-filled space within an animal's nose.

The term "central nervous system" means the part of the nervous system in vertebrates that comprises the brain and spinal cord, to which sensory impulses are transmitted and from which motor impulses pass out, and which coordinates the activity of the entire nervous system. In particular, the term "central nervous system" includes the olfactory bulb, left brain hemisphere, right brain hemisphere, cerebellum, and brain stem as well as their substructures. It also may include the cervical nodes, superficial and axillary nodes.

The term "animal" means any member of the kingdom Animalia which has a central nervous system and which normally has an air filled nasal cavity and includes humans.

The therapeutic composition, comprised of an antibody or antibody fragment linked to a polypeptide, may be administered by a wide variety of methods, and some exemplary methods are provided below. Absorption of the fusion polypeptide once introduced into the nasal cavity may occur via absorption across the olfactory epithelium, which is found in the upper one-third of the nasal cavity. Absorption may also occur across the nasal respiratory epithelium, which is innervated with trigeminal nerves, in the lower two-thirds of the nasal cavity. The trigeminal nerves also innervate the conjunctive, oral mucosa, and certain areas of the dermis of the face and head, and absorption after intranasal administration of the fusion polypeptide from these regions may also occur.

One exemplary formulation for intranasal delivery of the fusion polypeptide is a liquid preparation, preferably an aqueous based preparation, suitable for application as drops into the nasal cavity. For example, nasal drops can be instilled in the nasal cavity by tilting the head back sufficiently and apply the drops into the nares. The drops may also be inhaled through the nose.

Alternatively, a liquid preparation may be placed into an appropriate device so that it may be aerosolized for inhalation through the nasal cavity. For example, the therapeutic agent may be placed into a plastic bottle atomizer. In one embodiment, the atomizer is advantageously configured to allow a substantial amount of the spray to be directed to the upper one-third region or portion of the nasal cavity. Alternatively, the spray is administered from the atomizer in such a way as to allow a substantial amount of the spray to pass the nasal valve and to be directed to the upper one-third region or portion of the nasal cavity. By "substantial amount of the spray" it is meant herein that at least about 50%, further at least about 70%, but preferably at least about 80% or more of the spray passes the nasal valve and is directed to the upper and distal portion of the nasal cavity with about 10% or more reaching the upper third of the nasal cavity.

Additionally, the liquid preparation may be aerosolized and applied via an inhaler, such as a metered-dose inhaler. One example of a preferred device is that disclosed in U.S. Pat. No. 6,715,485 to Djupesland, and which involves a bi-directional delivery concept. In using the device, the end of the device having a sealing nozzle is inserted into one nostril and the patient or subject blows into the mouthpiece. During exhalation, the soft palate closes due to positive pressure thereby separating the nasal and oral cavities. The combination of closed soft palate and sealed nozzle creates an airflow in which drug particles are released entering one nostril, turning 180 degrees through the communication pathway and exiting through the other nostril, thus achieving bi-directional flow.

The fusion polypeptide can also be delivered in the form of a dry powder, as in known in the art. An example of a suitable device is the dry powder nasal delivery device marketed under the name DIRECTHALER™ nasal, and which is disclosed in PCT publication No. 96/222802. This device also enables closing of the passage between the nasal and oral cavity during dose delivery. Another device for delivery of a dry or liquid preparation is the device sold under the trade designation OPTINOSE™.

One embodiment of the invention is a method of delivering a catalytically active peptide chain or a peptide chain comprising an antibody Fc or Fab fragment to the central nervous system of an animal comprising providing a permeation enhancer in a concentration sufficient to enhance intranasal administration of the catalytically active peptide chain or peptide chain comprising an antibody Fc or Fab fragment to the central nervous system of an animal; and administering the pharmaceutical composition to the nasal cavity of an animal; whereby the catalytically active peptide chain or a peptide chain comprising an antibody Fc or Fab fragment enters the central nervous system of the animal. A pharmaceutical composition of the invention can be administered to the nasal cavity of an animal in the form of nasal drops, aerosol preparations, and the like as discussed above. A cannula or other device, such as the DIRECTHALER™ or OPTINOSE™ devices, can be used in the methods of the invention to facilitate the dispersion and nasal delivery of the pharmaceutical compositions of the invention. In the methods of the invention the animal can be a rodent, primate, human or other animal with a nasal cavity.

Another embodiment of the invention is a method of delivering a catalytically active peptide chain or a peptide chain comprising an antibody Fc or Fab fragment to the central nervous system of an animal comprising providing a pharmaceutical composition of the invention; and administering the pharmaceutical composition to the nasal cavity of an animal; whereby the catalytically active peptide chain or the peptide chain comprising an antibody Fc or Fab fragment enters the central nervous system of the animal.

Another embodiment of the invention is a method of delivering a peptide chain comprising an antibody Fc fragment to the central nervous system of an animal comprising providing a pharmaceutical composition of the invention wherein the peptide chain comprising the antibody Fc fragment binds to a melanocortin 4 receptor comprising the amino acid sequence shown in SEQ ID NO: 2; and administering the pharmaceutical composition to the nasal cavity of an animal; whereby the peptide chain comprising the antibody Fc fragment enters the central nervous system of the animal.

Another embodiment of the invention is a method of delivering a peptide chain comprising an antibody Fc fragment to the central nervous system of an animal comprising providing a pharmaceutical composition of the invention wherein the peptide chain comprising the antibody Fc fragment comprises the amino acid sequence shown in SEQ ID NO: 3; and administering the pharmaceutical composition to the nasal cavity of an animal; whereby the catalytically active peptide chain or a peptide chain comprising the antibody Fc fragment enters the central nervous system of the animal.

C. Methods of Treatment

In yet another aspect, methods of treatment are provided. The treatment methods may advantageously be utilized to treat a disorder in a mammal that is amenable to treatment by administration of a therapeutic agent to the central nervous system, such as the brain and/or spinal cord. That is, the disorder is one where the symptoms decrease or are otherwise eliminated, the rate of progression of the disorder decreases, and/or the disorder is eliminated by an agent that acts on the central nervous system.

In one embodiment, a method includes administering to the nasal cavity of a mammal, such as to cells and/or tissue in a region or portion of the nasal cavity of a mammal occupied by the superior turbinates, a therapeutically effective amount of an antibody fragment linked or otherwise conjugated to a polypeptide.

The method may be used to treat a wide variety of disorders. Suitable disorders include, for example, neurological and neurodegenerative disorders such as Alzheimer's disease, Parkinson's disease, and Huntington's disease, as well as other disorders known to the art that cause a loss of memory, such as multi-infarct dementia, Creutzfeldt-Jakob disease, Lewy body disease, normal pressure hydrocephalus and HIV dementia; or a loss of locomotion, such as stroke, amyotropic lateral sclerosis, myasthenia gravis and Duchenne dystrophy; endocrine, metabolic or energy balance disorders, such as obesity, diabetes and sleeping disorders, including insomnia; autoimmune disorders, such as multiple sclerosis; anorexia and treatment of acute injury from stroke or spinal cord injuries.

In one embodiment, a method of delivering a therapeutic composition to the central nervous system of a mammal includes administering the composition to the mammal intranasally, preferably to olfactory and/or trigeminal nerve endings, cells and nasal epithelium in a region of the nasal cavity located in the superior turbinates. This region or area is typically located in, but is not limited to, the upper one-third portion of the nasal cavity.

Although not being limited to any theory by which the method achieves its advantageous results, the agents that are applied intranasally according to the methods described herein may reach the brain directly by an extracellular or intracellular pathway. See, e.g., Thorne, R. G. et al., *Neuroscience,* 127:481-496 (2004). Intracellular pathways include transport through olfactory sensory neurons. This may involve, for example, absorptive or receptor-mediated endocytosis into olfactory sensory neurons and subsequent transport to olfactory bulb glomeruli. As another example, such transport may involve intraneuronal transport within the trigeminal nerve such that the composition is delivered to trigeminal ganglion and parts of the trigeminal brainstem nuclear complex, such as the subnucleus caudalis. In such intracellular pathways, the therapeutic agent may first be transported though nasal mucosa. Although antibody fragments that include the Fc portion (constant region) of an immunoglobulin may also be delivered by one of the aforementioned routes, one of the delivery routes may include being taken up by cells in the nasal mucosal epithelium having neonatal Fc receptors (FcRn) which may, depending on the mechanism, facilitate or hinder transport of the composition across the olfactory epithelium.

Extracellular pathways of entry of the composition into the central nervous system via the nasal cavity include direct entry into the cerebrospinal fluid, entry into the CNS parenchyma through extracellular spaces and channels, tracts or compartments associated with the olfactory system, such as the peripheral olfactory system, including the system that connects the nasal passages with the olfactory bulbs and rostral brain areas; and entry into the CNS parenchyma through extracellular spaces and channels, tracts or compartments associated with the trigeminal system, such as the peripheral trigeminal system, including the system connecting the nasal passages with the brainstem and spinal chord (Thorne, R. G. et al., *Neuroscience* 127:481-496 (2004)). Direct transport as used herein includes transport via one or more of the non-systemic pathways described herein.

Transport of the composition directly to the central nervous system by one or more of the mechanisms described herein allows the blood-brain barrier to be bypassed and overcomes the associated challenges and disadvantages surrounding systemic transport of agents to the central nervous system. Additionally, transporting the compositions by the methods described herein may allow less of the composition to be used as a greater proportion of the administered dose reaches the central nervous system target. In the case of administration of agents that are endogenously produced in the subject treated, the physiologic effects are typically comparable to the endogenous agent.

A therapeutically effective amount of the therapeutic composition is provided. As used herein, a therapeutically effective amount of the composition is the quantity of the composition required to achieve a specific therapeutic effect. For example, the amount is typically that required to reach a specified or desired clinical endpoint, such as a decrease in the progression of the disorder, a lessening of the severity of the symptoms of the disorder and/or elimination of the disorder. This amount will vary depending on the time of administration, the route of administration, the duration of treatment, the specific composition used and the health of the patient as known in the art. The skilled artisan will be able to determine the optimum dosage.

By intranasally administering the compositions by the methods described herein, it is realized that a smaller amount of the composition may be administered compared to systemic administration, including intravenous, oral, intramuscular, intraperitoneal, transdermal, etc. The amount of active agent and/or compositions required to achieve a desired clinical endpoint or therapeutic effect when intranasally administered as described herein may be less compared to systemic administration. Additionally, upon administering the compositions intranasally in the delivery and treatment methods described herein, about 5-fold to about 500-fold, and further about 10-fold to about 100-fold, less systemic exposure may be obtained compared to administration of the same amount systemically. Furthermore, at least about 5-fold, further at least about 10-fold, preferably at least about 20-fold and further at least about 50-fold less systemic exposure may be obtained compared to administration of the same amount systemically. In determining the therapeutic effectiveness of the compositions, clinical endpoints known to the art for the particular disorder may be monitored. For example, suitable clinical endpoints for dementia and Alzheimers' disease include, for example, improved cognitive function, decreases in memory loss, language deterioration, confusion, restlessness and mood swings; and improved ability to mentally manipulate visual information as determined by standard methods.

Suitable clinical endpoints for Huntington's disease include a decrease in uncontrolled movements, and an improvement or no further decrease of intellectual faculties.

Suitable clinical endpoints for Parkinson's disease include, for example, a decrease in the characteristic tremor (trembling or shaking) of a limb, especially when the body is at rest, an increase in movement (to help overcome bradykinesia), improved ability to move (to help overcome akinesia), less rigid limbs, improvement in a shuffling gait, and an improved posture (correcting the characteristic stooped posture). Such clinical endpoints may be observed by standard methods. Other suitable clinical endpoints include a decrease in nerve cell degeneration and/or no further decline in nerve cell degeneration and may be observed, for example, by brain imaging techniques, including computer assisted tomography (CAT) scanning, magnetic resonance imaging methods, or similar methods known to the art.

Suitable clinical endpoints for obesity include, for example, a decrease in body weight, body fat, food intake or an increase in lean body mass, metabolic rate or a combination thereof.

Suitable clinical endpoints for sleep disorders, such as insomnia, include, for example, an improvement in the ability to sleep, and especially improved rapid eye movement (REM) sleep.

Suitable clinical endpoints for autoimmune disorders such as multiple sclerosis include, for example, a decrease in the number of brain lesions, increased extremity strength or a decreased in tremors or paralysis of extremities. Decreases in the number of brain lesions may be observed by brain imaging techniques previously described herein. Other suitable clinical endpoints include a decrease in inflammation of nervous tissue which may be determined by, for example, lumbar puncture techniques and subsequent analysis of cerebrospinal fluid known to the art.

In individuals who have experienced a stroke, a suitable clinical endpoint includes an increase in blood flow in the affected blood vessel as determined by computer tomographic methods as known in the art and as described, for example, in Nabavi, D. G., et al., *Radiology* 213:141-149 (1999). A further clinical endpoint includes a decrease in numbness in the face, arm or leg; or a decrease in the intensity of a headache associated with the stroke. Yet another clinical endpoint includes a decrease in the cell, tissue or organ damage or death due to the stroke. Such decrease in cell or tissue damage may be assessed by brain imaging techniques previously described herein, or similar methods known to the art.

Suitable clinical endpoints in neuropsychologic disorders such as schizophrenia include, for example, improvements in abnormal behavior, and a decrease in hallucinations and/or delusions.

The patient or subject treated according to the methods of the present invention is typically one in need of such treatment, including one that has a particular disorder amenable to treatment by such methods. The patient or subject is typically a mammal, such as a human, although other mammals may also be treated.

EXAMPLES

Reference will now be made to specific illustrative examples. It is to be understood that the examples are provided to illustrate preferred embodiments and that no limitation to the scope is intended thereby. Additionally, all documents cited herein are indicative of the level of skill in the art and are hereby incorporated by reference in their entirety.

Example 1

Brain Distribution of α-Melanocyte Stimulating Hormone Mimetibody after Intranasal Administration This example shows that an α-melanocyte stimulating hormone mimetibody (α-MSH mimetibody) is transported to various regions in the brain and was detected at about 25 minutes after intranasal administration while reducing systemic exposure according to the methods of the present invention. The example further shows that the α-MSH mimetibody delivered to the brain is retained in the brain for at least up to 5 hours post-delivery.

Methods

An α-MSH mimetibody was prepared, to serve as a model and exemplary therapeutic compound to illustrate the claimed method. The α-MSH mimetibody is a homo-dimeric fusion molecule that consists of the therapeutic α-MSH polypeptide, identified herein as SEQ ID NO:1, and the Fc portion of the human immunoglobulin G1 (IgG1) monoclonal antibody. The engineered fusion polypeptide was produced using recombinant DNA methods.

The α-MSH mimetibody was iodinated by Amersham Biosciences's Iodine-125 Custom Labeling Services using the Chloramine T method. $^{125}$I-labeled α-MSH mimetibody, together with unlabeled α-MSH mimetibody as a cold carrier, was intranasally or intravenously administered to eight anesthetized rats (Sprague Dawley, 200-250 g). Intranasal drug administration was performed in the fume hood behind a lead-impregnated shield. Each rat was placed on its back on a heating pad with a 37° C. rectal probe; the rat's head was slightly elevated by rolled-up 4×4 gauze. The unlabeled mimetibody, dissolved in PBS, was spiked with 39 µCi of $^{125}$-I labeled α-MSH mimetibody. A total volume of 100 µl containing approximately 13 nmol or 0.8 mg of α-MSH mimetibody was administered in 10 µl nose drops to alternating nares every two minutes over a 15-20 minute time period to young male rats while under anesthesia and lying on their back. For intravenous administration, $^{125}$I-labeled α-MSH mimetibody was delivered as a bolus injection through the tail vein in a total volume of 0.5 ml (diluted in saline). Rats were administered either a full dose (equivalent to intranasal) or $\frac{1}{10}^{th}$ of the intranasal dose (0.08 mg or 1.3 nmol α-MSH mimetibody containing 39 µCi). Blood samples were taken every 5 minutes up to 25 minutes. At about 27 minutes or 5 hours after the beginning of drug administration, the rats were perfused to remove blood-borne label and fixed.

The distribution of $^{125}$I-labeled α-MSH mimetibody in the CNS and peripheral organs was assessed following intranasal or intravenous delivery in rats. Tissue pieces from the brain, organs and peripheral tissues were carefully excised, weighed and gamma-counted. Concentrations of α-MSH mimetibody were assessed using either gamma counting (quantitative analysis) or by autoradiography of coronal brain section (qualitative analysis). The nanomolar concentration in each tissue piece and in the blood was determined based on the amount of counts per tissue weight and specific activity of the radio-labeled protein.

Results

As seen in FIG. 1, the $^{125}$I-labeled α-MSH mimetibody can be detected in various CNS tissues after intranasal delivery into young male rates within 25 minutes after administration. FIG. 1 further shows that most of the $^{125}$I-labeled α-MSH mimetibody is retained at 5 hours post-intranasal delivery, suggesting that the half-life of α-MSH mimetibody is greater than 5 hours. It is more specifically seen that the $^{125}$I-labeled α-MSH mimetibody reached the hypothalamus, the target site for action of the α-MSH peptide (binding to MCR4 on hypothalamic neurons). In addition, the hypothalamus (3 nM of mimetibody) is targeted with intranasal delivery although there is significant delivery to all brain regions, especially the medulla, pons and frontal cortex.

Table 1 further compares the distribution of $^{125}$I-labeled α-MSH mimetibody administered intranasally and intravenously.

TABLE 1

Distribution of α-MSH Mimetibody After Intranasal and Intravenous Delivery

| Tissue | Average Concentration of αMSH-Mimetibody (nM) | |
|---|---|---|
| | Intranasal (13 n mol) | Intravenous (1.3 n mol) |
| blood sample 1 (5 min) | 0.5 +/− 0.1 | 33.4 +/− 2.97 |
| blood sample 2 (10 min) | 1.6 +/− 0.2 | 35.5 +/− 3.18 |
| blood sample 3 (15 min) | 2.9 +/− 0.4 | 32.1 +/− 2.83 |
| blood sample 4 (20 min) | 4.6 +/− 0.7 | 34.1 +/− 3.0.4 |
| blood sample 5 (25 min) | 5.4 +/− 0.8 | 28.2 +/− 2.59 |
| olfactory epithelium | 17.1 +/− 1.6 | 1.8 +/− 0.16 |
| olfactory bulb | 16.2 +/− 5 | 0.2 +/− 0.02 |
| trigeminal nerve | 19.1 +/− 3.4 | 0.5 +/− 0.03 |
| frontal cortex | 1.3 +/− 0.3 | 0.2 +/− 0.02 |
| Medulla | 1.8 +/− 0.4 | 0.1 +/− 0.01 |
| Hypothalamus | 3.0 ± 0.4 | 0.4 ± 0.06 |
| Liver | 1.8 +/− 1.0 | 18.9 +/− 1.59 |
| Kidney | 3.3 +/− 0.5 | 5.7 +/− 0.58 |
| Spleen | 1.2 +/− 0.2 | 3.9 +/− 0.76 |

Intravenous delivery also targets the hypothalamus. However, despite the 13.5 higher blood exposure (AUC) with intravenous administration (see Table 1 and FIGS. 1 and 2), intranasal administration results in greater CNS delivery. Delivery of the peptide to the hypothalamus, frontal cortex, and medulla were 7.5, 6.5 and 18 fold higher, respectively, with intranasal than intravenous administration.

Table 2 shows the relative effectiveness of intranasal (i.n.) and intravenous (i.v.) delivery by comparing various ratios of polypeptide tissue concentrations. Specifically, the ratio of polypeptide concentration in the hypothalamus to polypeptide concentration in the blood at 25 minutes post delivery is shown in Table 2, for both intranasal and intravenous delivery. The ratio of polypeptide concentration in the hypothalamus to polypeptide concentration in the liver at 25 minutes post delivery is also shown in Table 2, for both intranasal and intravenous delivery. Intranasal delivery was significantly more effective, as evidenced by the 48 and 75 fold ratios, to deliver the polypeptide to the hypothalamus than was intravenous delivery.

TABLE 2

Relative effectiveness of intranasal and intravenous delivery in targeting the hypothalamus

| | i.n.* | i.v* | Ratio (i.n.)/(i.v.) |
|---|---|---|---|
| [polypeptide]$_{hypothalamus}$/[polypeptide]$_{blood}$ | 0.558 | 0.012 | 48 |
| [polypeptide]$_{hypothalamus}$/[polypeptide]$_{liver}$ | 1.640 | 0.022 | 75 |

*i.n. = intranasal; i.v. = intravenous

Figure 2:
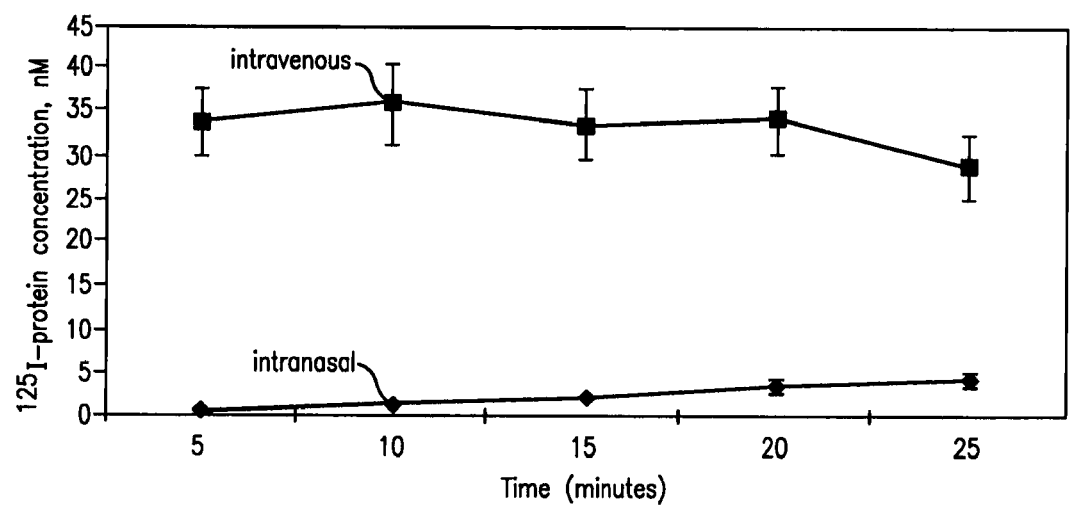
FIG. 2 is a graph showing the blood concentration of $^{125}$I-α-MSH mimetibody, in nmol, after intranasal (diamonds) or intravenous (squares) administration of $^{125}$I-α-MSH mimetibody to rats, as a function of time post delivery, in minutes, as more fully described in Example 1.

The data in Table 1 and FIG. 2 also show that systemic exposure of the $^{125}$I-labeled α-MSH mimetibody was low when administered intransally. An intranasal one-tenth the amount of the intravenous dose resulted in a 13.5-fold lower systemic exposure, based on the blood AUC(intravenous)/AUC(intranasal) ratio, and a 10.5-fold lower exposure based on a ratio of liver protein concentration when dosed intravenously to the liver protein concentration when dosed intranasally. Further, a consistent depot of the mimetibody (17.1+/− uM) was created in the olfactory epithelium across the 14 animals (see Table 1 above), and olfactory and trigeminal pathway concentrations of the test protein were similar upon intranasal administration indicating that the protein travels to the CNS via the olfactory and trigeminal neural pathways. Comparing equal intranasal and intravenous doses, systemic exposure was about 96-fold lower based on blood AUC(i.v.)/AUC(i.n.) ratio with approximately equal amounts of protein delivered to the CNS and hypothalamus.

Figure 3:
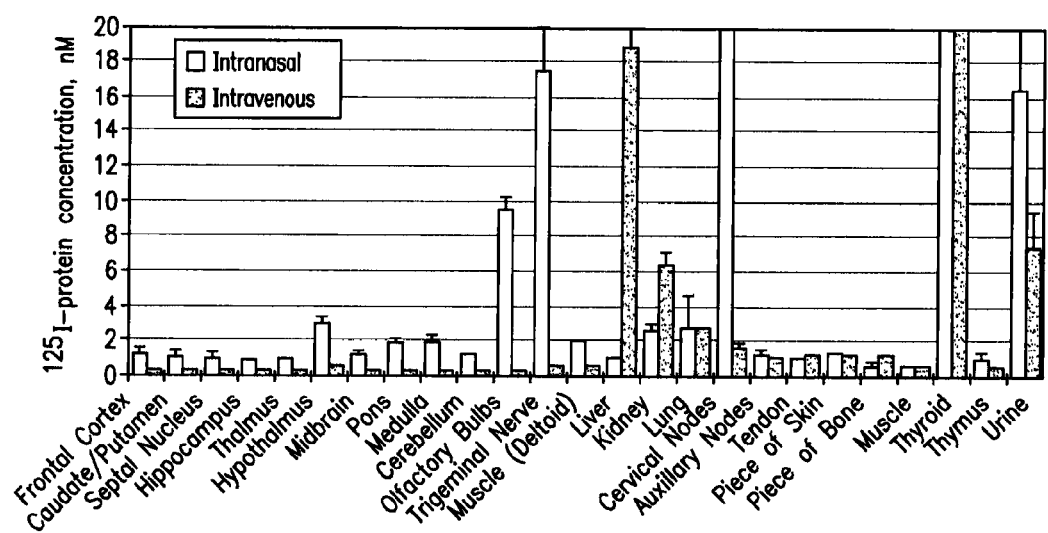
FIG. 3 is a graph comparing the distribution of $^{125}$I-α-MSH mimetibody in the central nervous system and peripheral tissues of rats after either intranasal (open bars) or intravenous (dotted bars) administration of $^{125}$I-α-MSH mimetibody, as more fully described in Example 1.

FIG. 3 shows that delivery of the $^{125}$I-labeled α-MSH mimetibody to the central nervous system is unlikely to be secondary through the blood. For example, as seen in FIG. 3, when rats are exposed to a 10-fold higher dosage of $^{125}$I-labeled α-MSH mimetibody by intranasal administration compared to intravenous administration, there was a higher accumulation of the $^{125}$I-labeled α-MSH mimetibody in the central nervous system by intranasal administration.

Figure 4A:
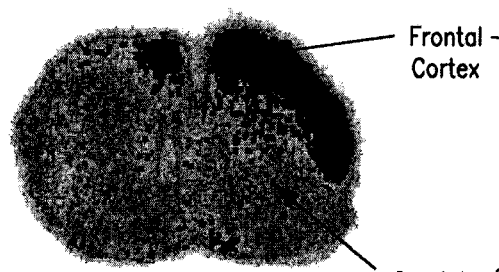
FIGS. 4A-4D show computer-generated autoradiographs of coronal sections of rat brains 25 minutes after administration of $^{125}$I-α-MSH mimetibody either intranasally (FIGS. 4A, 4C) or intravenously (FIGS. 4B, 4D), as more fully described in Example 1.
Figure 4B:
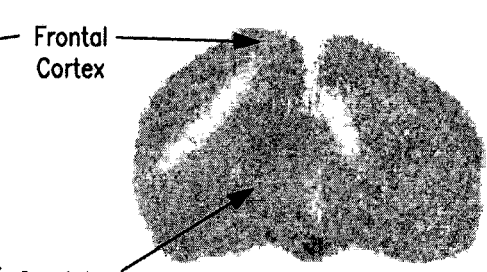
Figure 4C:
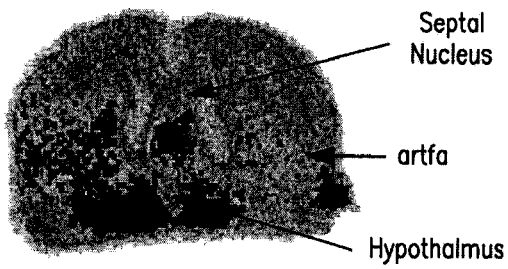
Figure 4D:
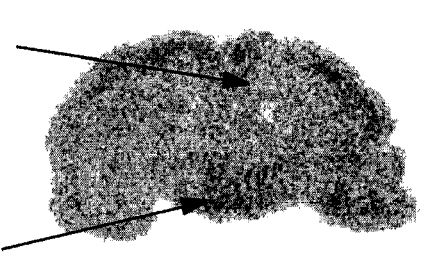

FIGS. 4A-4D show computer-generated autoradiographs of coronal sections of the rat brains 25 minutes after administration of $^{125}$I-α-MSH mimetibody intranasally (FIGS. 4A, 4C) or intravenously (FIGS. 4B, 4D). The darkened area in the autoradiographs corresponds to the regions of high image intensity, which correlates to regions of fusion polypeptide delivery. As seen in FIGS. 4A, 4C, which correspond to the animals treated intranasally, the highest image intensities were observed in the olfactory tracts, hypothalamus, and frontal cortex. These images confirm findings from quantitative measurements.

Example 2

Dose-Dependent Reduction in Cumulative Food Intake in Normal Rats after Intranasal Administration of Alpha-MSH This example shows that intranasal administration of a single dose of the N-acetylated α-melanocyte stimulating hormone (Ac-Ser-Tyr-Ser-Met-Glu-His-Phe-Arg-Trp-Gly-Lys-Pro-Val-NH2, SEQ ID NO:1, supplied by Phoenix Pharmaceuticals, INC) was sufficient to achieve a dose dependent, pharmacodynamic response; specifically, a reduction of cumulative food intake, with an $ED_{50}$ at 24 hours of 6-7 nmol.

1. Methods

Two groups of nine rats each were assembled. In a crossover design, each week one group was dosed with a phosphate buffered saline (PBS) vehicle and the other group was dosed with α-MSH peptide; the following week the treatment administered to each group was reversed. Prior to the study, the light cycle was slowly reversed, within a 2 weeks acclimation period. Rats were fasted for 24 hours prior to each experiment (water was always available), and received anesthesia 30 minutes prior to the beginning of the dark cycle (or the period of lights off). A single dose of drug ranging from 2.5 to 50 nmols or phosphate-saline buffered vehicle control was intranasally administered during anesthesia over approximately 20 minutes, similar to the procedure set forth in Example 1. Rats were placed on their backs on a heating pad and monitored until they become active, and then were placed in their cages with pre-weighed amounts of food. Food intake measurements were taken at 2, 4, 8, 24, 48 and 72 hours. Water intake and body weight were determined at 24 and 48 hours post-dosing.

Results and Conclusions

Figure 5:
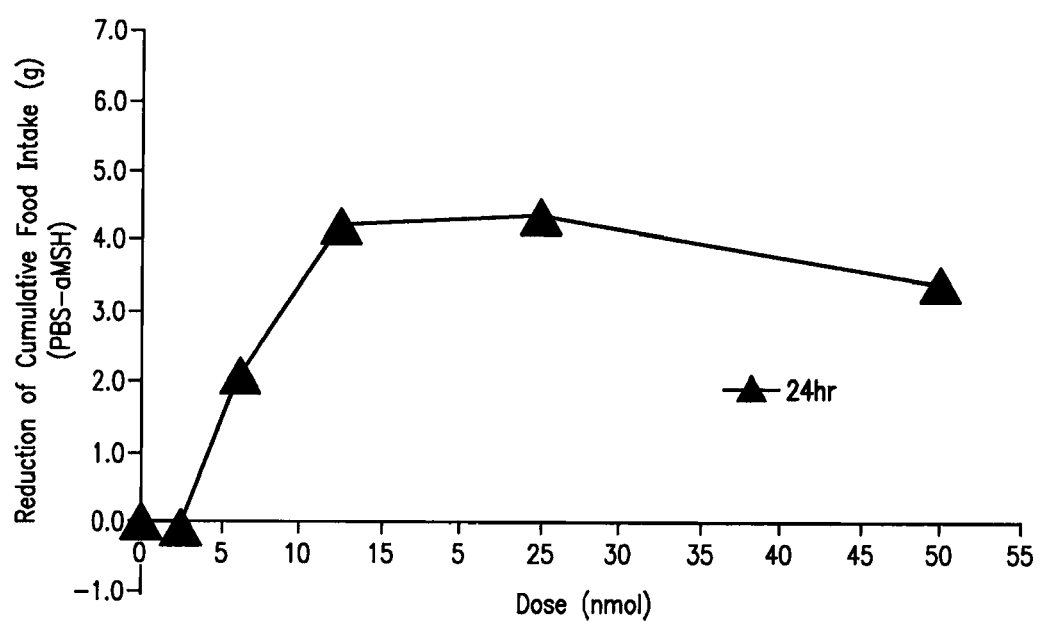
FIG. 5 is a graph showing the reduction of cumulative food intake in rats, in grams, 24 hours after intranasal treatment with α-MSH mimetibody at varying doses, in nmol.

As seen in FIG. 5, intranasal α-MSH peptide reduces cumulative food intake dose dependently between 2.5-25 nmols at 24 hours with an $ED_{50}$ at 6-7 nmols.

Figure 6:
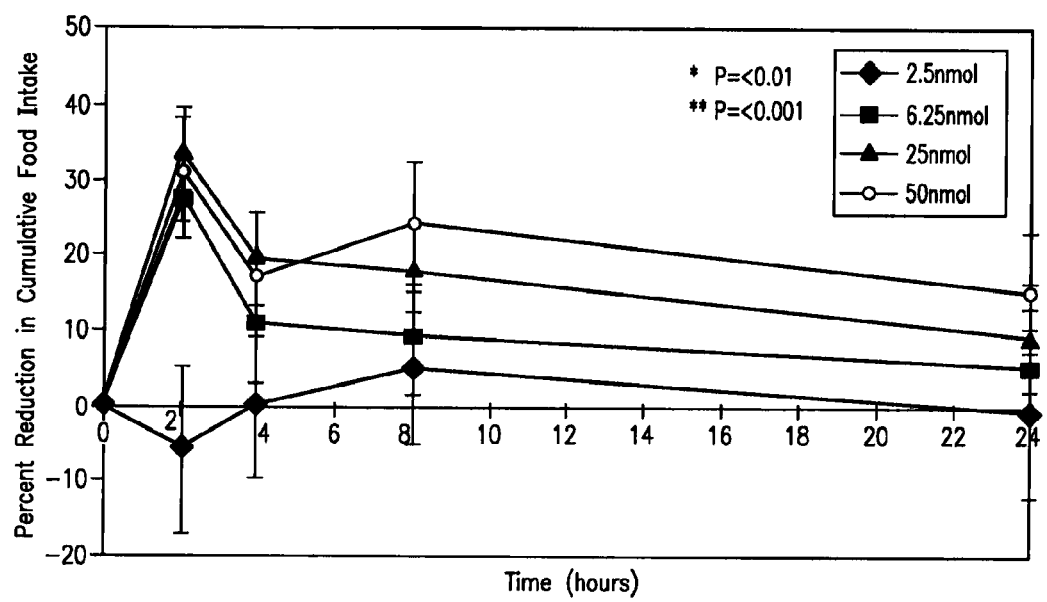
FIG. 6 is a graph showing the percentage reduction in cumulative food intake in rats, as a function of time, in hours, after intranasal treatment with α-MSH mimetibody at a dose of 2.5 nmol (diamonds), 6.25 nmol (squares), 25 nmol (triangles), or 50 nmol (circles)

As shown in FIG. 6, a single dose of 25-50 nmol was maximally effective in reducing percent cumulative food intake. The 25 nmol dose reduced cumulative food consumption by 30% at 2 hours, by 18% at 8 hours, and by 9% at 24 hours. Water consumption and body weight remained unchanged. This study shows a dose dependent pharmacodynamic effect of a polypeptide after intranasal administration to a mammal.

Example 3

Reduction in Cumulative Food Intake in Normal Rats after Intranasal Administration of Alpha-MSH Mimetibody This example shows that intranasal administration of a single dose of 25 nmols (5 mg/kg) of the α-MSH mimetibody is sufficient to reduce cumulative food intake significantly at 8 and 24 hours. Water consumption and body weight remained unchanged.

1. Methods

The study protocol and methods used were the same as described in Example 2. The total number of rats was 14.

2. Results and Conclusions

Figure 7:
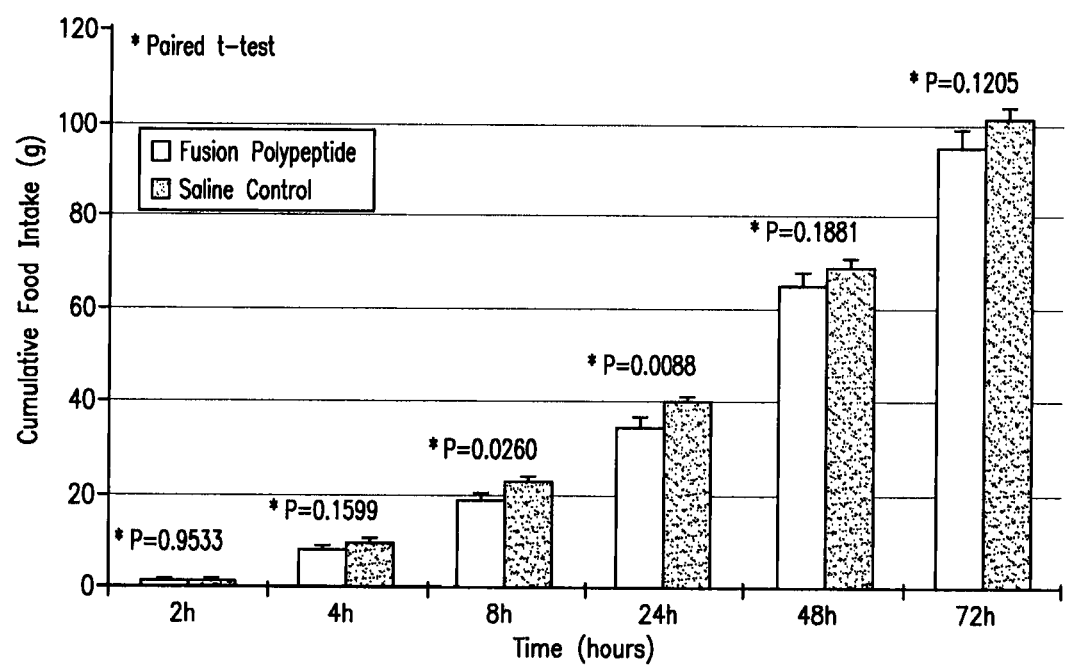
FIG. 7 is a bar graph showing the cumulative food intake in rats, in grams, at the indicated times post treatment with α-MSH mimetibody (open bars) or saline (dotted bars) administered intranasally.

As seen in FIG. 7, a single dose of 25 nmol of intranasally delivered alpha-MSH mimetibody had a significant effect on decreasing cumulative food intake at 8 and 24 hours, with a non-statistically significant trend toward reduction at 48 and 72 hours. The significance at the later time points was likely lost due to the relatively small number of animals used in the study (n=14). The study shows that a 62 kDa large protein, like the α-MSH mimetibody, can be delivered to the CNS via the nasal route of administration.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Example 4

Figure 8:
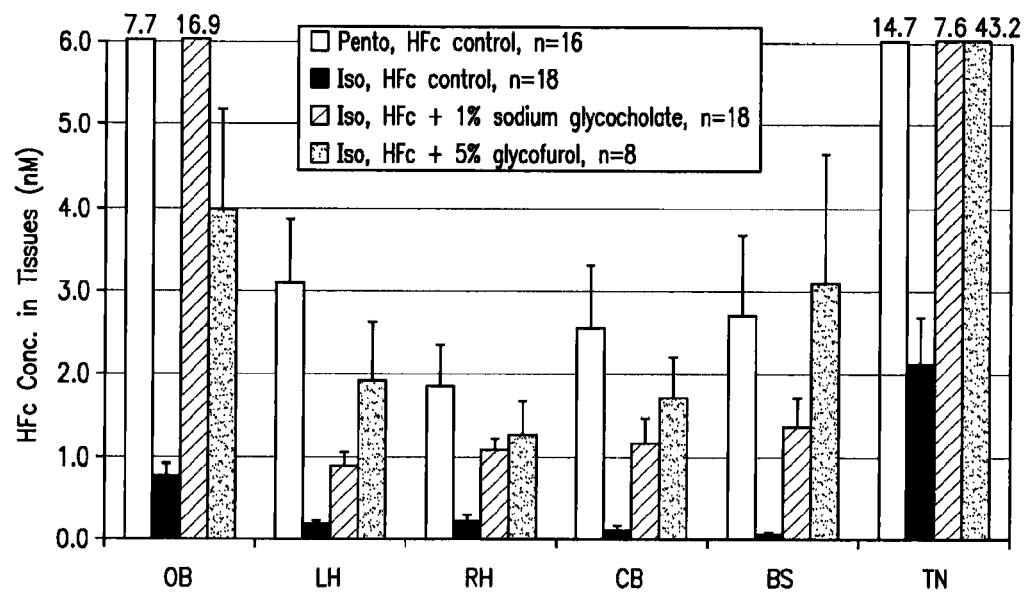
FIG. 8 is a bar graph showing increased antibody fragment delivery to central nervous system tissues in isoflurane anesthetized rats after nasal administration of hFc formulations comprising 5% (v/v) tetrahydrofurfuryl-polyethyleneglycol or 1% (w/v) sodium glycocholate hydrate.

Nasal Administration of Formulations Comprising 5% (v/v) Tetrahydrofurfuryl-Polyethylenglycol or 1% (w/v) Sodium Glycocholate Hydrate Increase Antibody Fragment Delivery to Central Nervous System Tissues Nasal administration of a *Homo sapiens* derived antibody Fc fragment (hFc) to central nervous system (CNS) tissues was increased, relative to controls, by inclusion of either 5% (v/v) tetrahydrofurfuryl-polyethylenglycol or 1% (w/v) sodium glycocholate hydrate in the hFc formulation (FIG. 8).

A rat model was used for evaluating intranasal drug delivery to the brain. Male Sprague-Dawley rats were anesthetized with 40 mg of sodium pentobarbital (NEMBUTAL®) per kg of animal body weight administered intraperitoneally (i.p.) or 3.0% isoflurane inhalant to facilitate nasal administration of the liquid formulations comprising hFc. Anesthetized rats were placed on their backs and their necks were supported with a neck pillow to elevate their heads at which point 60 μL of the liquid formulations were administered drop-wise to alternating nostrils of each animal every 2 minutes as described by Thorne and Frey (Thorne et al, 127 *Neuroscience* 481 (2004)). A heating pad was used to maintain body temperature of anesthesized animals.

25 minutes after start of nasal administration of the hFc formulations animals were perfused via cardiac puncture with phosphate buffered saline (PBS) containing protease inhibitors (1 protease inhibitor cocktail tablet/Roche per 10 ml of PBS) and 5 nM EDTA tetrasodium salt. Brains and other tissues were dissected and collected for analysis of hFc content. Blood was collected prior to the study, which was typically one day prior to nasal administration of the hFc formulations, and prior to the start of perfusion. Tissues were homogenized in a homogenization buffer containing protease inhibitors (1 protease inhibitor cocktail tablet/Roche per 10 ml of PBS), 5 nM EDTA tetrasodium salt, and 1% (v/v) Tween 20. Homogenized tissue samples or blood were then centrifuged and supernatants were collected for hFc assays. hFc concentrations were determined in tissue homogenate and blood plasma samples, using standard ELISA assay techniques specific for *Homo sapiens* antibody Fc chains of the IgG1 isotype.

hFc is a *Homo sapiens* antibody fragment comprising a Fc fragment of the IgG1 isotype and has a molecular weight of 52,862 Dal and was purified using standard techniques after expression by eukaryotic cells.

Control hFc formulations comprised 30 mg/ml hFc in PBS at pH 7.4. Tetrahydrofurfuryl-polyethylenglycol comprising hFc formulations contained 5% (v/v; e.g. 5 ml tetrahydrofurfuryl-polyethylenglycol diluted to 100 ml PBS buffer) tetrahydrofurfuryl-polyethylenglycol in PBS buffer at pH 7.4 and 30 mg/ml hFc. Sodium glycocholate hydrate comprising hFc formulations contained 1% (w/v; e.g. 1 g of 97% pure sodium glycocholate hydrate in 100 ml of PBS buffer diluent) sodium glycocholate hydrate in PBS buffer at pH 7.4 and 30 mg/ml hFc.

Percent (w/v) and percent (v/v) values reported herein are uncorrected for the purity by mass or volume of a given compound in a formulation. For example, 100 ml of a 1% (w/v) sucrose solution made from a 97% pure sucrose preparation would contain only 0.97 gram of sucrose in 100 ml. This reflects the practical fact that for many compound preparations the actual purity by mass or volume of a given compound in the preparation is not known with absolute certainty, but is instead only known within the limits of the assay techniques used. Furthermore, due to the heterogenous nature of some compounds such as polymers and hydrates it is often difficult to describe the purity of the compound by mass because the mass of the compounds in the preparation, such as polymers, or the mass and stoichiometry of hydrate in the preparation is variable or undetermined.

Sodium glycocholate hydrate was from Sigma-Aldrich (St. Louis, Mo.) and had a purity of greater than 97% by mass (Table 3). "Sodium glycocholate" is a shorthand designation or nomenclature used in the Figures, and Tables to refer to "sodium glycocholate hydrate."

Tetrahydrofurfuryl-polyethylenglycol was from Alchymars SpA (Milano, Italy) (Table 3). "Glycofurol" is a shorthand designation or nomenclature used in the Figures and Tables to refer to "tetrahydrofurfuryl polyethylenglycol."

As seen in FIG. 8, nasal administration of hFc formulations comprising 5% (v/v) tetrahydrofurfuryl-polyethylenglycol or 1% (w/v) sodium glycocholate hydrate to isoflurane anesthetized animals resulted in hFc concentrations in CNS tissues that were higher than those in isoflurane anesthetized animals receiving the control hFc formulation.

In FIG. 8 "sodium glycocholate" is used to designate "sodium glycocholate hydrate" and "glycofurol" is used to designate "tetrahydrofurfuryl-polyethylenglycol." Abbreviations used in FIG. 8 are as follows: "iso"=isoflurane; "pento"=pentobarbital; OB=olfactory bulb; LH=left brain hemisphere; RH=right brain hemisphere; CB=cerebellum; BS=brain stem; TN=trigeminal nerve. Error bars represent standard errors for a given data set. Mean values are indicated above off-scale bars as necessary. The number of animals in each group is as indicated in FIG. 8.

Example 5

Figure 9:
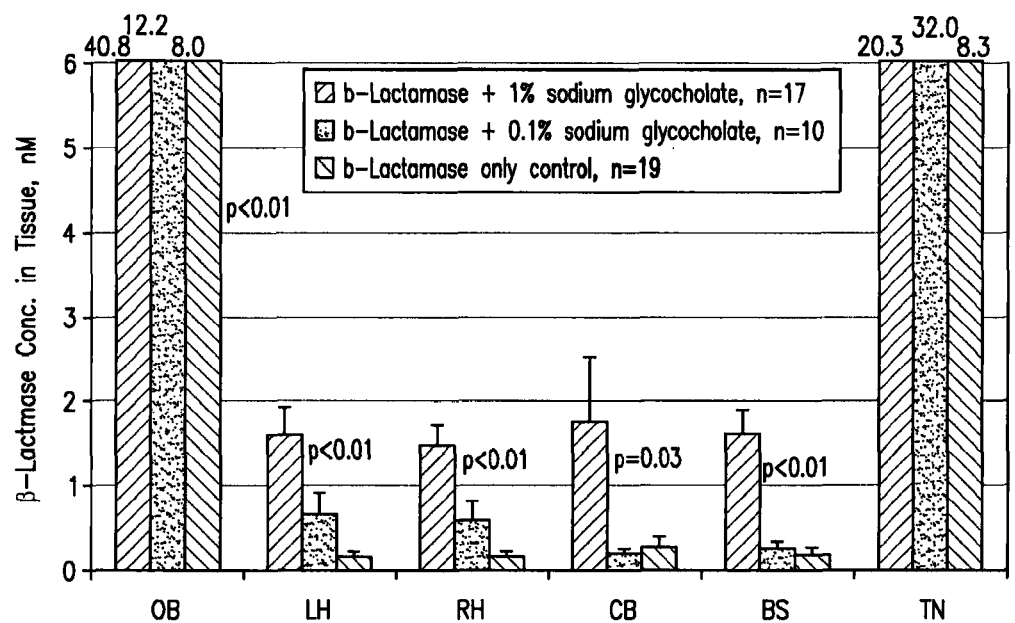
FIG. 9 is a bar graph showing that nasal administration of formulations comprising 1% (w/v) sodium glycocholate hydrate permits delivery of biologically active, high molecular weight enzymes to central nervous system tissues in isoflurane anesthetized animals.

Nasal Administration of Formulations Comprising 1% (w/v) Sodium Glycocholate Hydrate Permits Delivery of Biologically Active, High Molecular Weight Enzymes to Central Nervous System Tissues Nasal administration of a biologically active, high molecular weight enzyme to central nervous system (CNS) tissues was achieved (FIG. 9). As shown in FIG. 9, delivery of the 32,000 Da beta-lactamase enzyme to CNS tissues was increased, relative to controls, by the inclusion of 1% (w/v) sodium glycocholate hydrate in the nasally administered formulations comprising this enzyme (FIG. 9).

Formulations comprising the beta-lactamase enzyme were nasally administered to anesthetized rats using the methods described in Example 4 above; 60 µL of formulation was administered. Tissue and plasma samples were also prepared as described in Example 4. Beta-lactamase enzyme activity and concentrations were determined in tissue homogenate and blood plasma samples, using standard fluorescent substrate based assay techniques.

Beta-lactamase is an enzyme that hydrolyzes the beta-lactam ring in certain antibiotics containing beta-lactam rings (e.g. penicillin). Beta-lactamase has a molecular weight of about 32,000 Da.

Control beta-lactamase formulations comprised 20 mg/ml beta-lacatamase in PBS at pH 7.4. Sodium glycocholate hydrate comprising beta-lactamase formulations contained either 1% (w/v; e.g. 1 g of 97% pure sodium glycocholate hydrate in 100 ml of PBS buffer diluent) sodium glycocholate hydrate or 0.1% sodium glycocholate hydrate in PBS buffer at pH 7.4 and 20 mg/ml beta-lactamase. Percent (w/v) and percent (v/v) values reported herein are uncorrected for the purity by mass or volume of a given compound in a formulation.

Sodium glycocholate hydrate was from Sigma (St. Louis, Mo.) and had a purity of greater than 97% by mass (Table 3). "Sodium glycocholate" is a shorthand designation or nomenclature used in the Figures and Tables to refer to "sodium glycocholate hydrate."

As seen in FIG. 9, nasal administration of a biologically active, high molecular weight enzyme to central nervous system (CNS) tissues was achieved. Furthermore, nasal administration of beta-lactamase formulations comprising 0.1-1% (w/v) sodium glycocholate hydrate to isoflurane anesthetized animals resulted in beta-lactamase concentrations in CNS tissues that were higher than those in isoflurane anesthetized animals receiving the control beta-lactamase formulation in PBS only.

Abbreviations and compound designations used in FIG. 9 are the same as described for FIG. 8 in Example 4 above. Error bars represent standard deviations for a given data set. Mean values are indicated in FIG. 9 above off-scale bars as necessary. P-values used for statistical analyses are indicated in FIG. 9. The number of animals in each group is as indicated in FIG. 9.

Example 6

Figure 10:
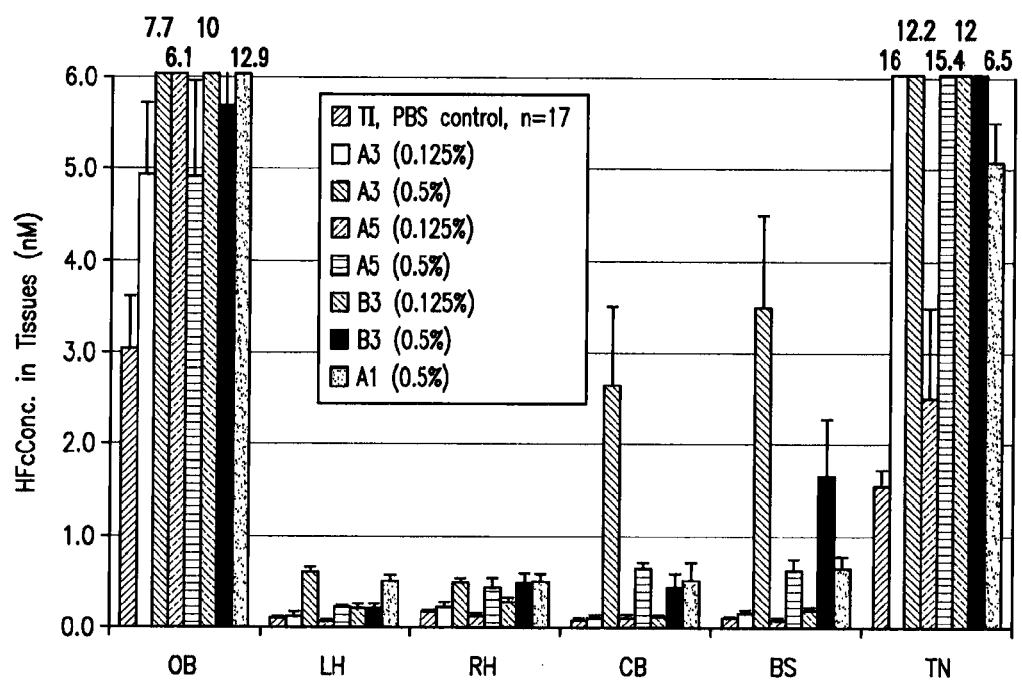
FIG. 10 is a bar graph showing increased antibody fragment delivery to central nervous system tissues in isoflurane anesthetized rats after nasal administration of hFe formulations comprising from 0.125% (w/v) to 0.5% (w/v) of 1-O-n-dodecyl-beta-D-maltopyranoside (designated A3), 1-O-n-decyl-beta-D-maltopyranoside (designated A1), 1-O-n-tetradecyl-beta-D-maltopyranoside (designated A5), and beta-D-fructopyranosyl-alpha-glucopyranosyl monododecanoate (designated B3).

Nasal Administration of Formulations Comprising from 0.125% (w/v) to 0.5% (w/v) of N-Decyl-Beta-D-Maltopyranoside, N-Dodecyl-Beta-D-Maltopyranoside, N-Tetradecyl-Beta-D-Maltopyranoside, or Beta-D-Fructopyranosyl-Alpha-Glucopyranoside Monododecanoate Increase Antibody Fragment Delivery to Central Nervous System Tissues Nasal administration of a *Homo sapiens* derived antibody Fc fragment (hFc) to central nervous system (CNS) tissues was increased, relative to controls, by inclusion of 0.125% (w/v) to 0.5% (w/v) of n-decyl-beta-D-maltopyranoside, n-dodecyl-beta-D-maltopyranoside, n-tetradecyl-beta-D-maltopyranoside, or beta-D-fructopyranosyl-alpha-glucopyranoside monododecanoate in the hFc formulation (FIG. 10).

A rat model was used for evaluating intranasal drug delivery to the brain. Male Sprague-Dawley rats were anesthetized with 3.0% isoflurane inhalant to facilitate nasal administration of the liquid formulations comprising hFc. Anesthetized rats were placed on their backs and their necks and head were supported with a platform to elevate their heads at a 45° angle. A micro-cannula was then inserted 1 cm into the right nostril of the animals and a 50 µL it bolus of the liquid formulations was administered over the span of 1 minute. A heating pad was used to maintain body temperature of anesthesized animals.

20 minutes after nasal administration of the hFc formulations, animals were perfused via cardiac puncture with phosphate buffered saline (PBS) containing protease inhibitors (1 Roche protease inhibitor cocktail tablet per 10 ml of PBS) and 5 nM EDTA tetrasodium salt. Brains, blood and other tissues were then dissected, collected, and analyzed for hFc content as described in Example 4 above.

Control hFc formulations comprised 36 mg/ml hFc in PBS at pH 7.4. n-decyl-beta-D-maltopyranoside comprising hFc formulations contained 0.125% (w/v) to 0.5% (w/v) of n-decyl-beta-D-maltopyranoside in PBS buffer at pH 7.4 and 36 mg/ml hFc. n-dodecyl-beta-D-maltopyranoside comprising hFc formulations contained 0.125% (w/v) to 0.5% (w/v) of n-dodecyl-beta-D-maltopyranoside in PBS buffer at pH 7.4 and 36 mg/ml hFc. n-tetradecyl-beta-D-maltopyranoside comprising hFc formulations contained 0.125% (w/v) to 0.5% (w/v) of n-tetradecyl-beta-D-maltopyranoside in PBS buffer at pH 7.4 and 36 mg/ml hFc. Beta-D-fructopyranosyl-alpha-glucopyranoside monododecanoate comprising hFc formulations contained 0.125% (w/v) to 0.5% (w/v) of beta-D-fructopyranosyl-alpha-glucopyranoside monododecanoate in PBS buffer at pH 7.4 and 36 mg/ml hFc. Percent (w/v) and percent (v/v) values reported herein are uncorrected for the purity by mass or volume of a given compound in a formulation.

n-decyl-beta-D-maltopyranoside (Table 3) was obtained from Aegis Therapeutics, LLC (San Deigo, Calif.). n-dodecyl-beta-D-maltopyranoside was obtained from Inalco SpA (Milano, Italy) and had a purity of greater than 99% by mass (Table 3). n-tetradecyl-beta-D-maltopyranoside was from Inalco SpA (Milano, Italy) and had a purity of greater than 99% by mass. Beta-D-fructopyranosyl-alpha-glucopyranoside monododecanoate was from Anatrace, Inc. (Maumee, Ohio) and had a purity of 98.90% by mass.

As seen in FIG. 10, nasal administration of hFc formulations comprising 0.125% (w/v) to 0.5% (w/v) of n-decyl-beta-D-maltopyranoside, n-dodecyl-beta-D-maltopyranoside, 1-O-n-tetradecyl-beta-D-maltopyranoside, or beta-D-fructopyranosyl-alpha-glucopyranoside monododecanoate to isoflurane anesthetized animals resulted in hFc concentrations in CNS tissues that were higher than those in isoflurane anesthetized animals receiving the control hFc formulation.

In FIG. 10, the designation "A1" is used for n-decyl-beta-D-maltopyranoside formulations. "A3" is used for n-dodecyl-beta-D-maltopyranoside formulations. "A5" is used for n-tetradecyl-beta-D-maltopyranoside. "B3" is used for beta-D-fructopyranosyl-alpha-glucopyranoside monododecanoate formulations. Otherwise, abbreviations and designations used in FIG. 10 are the same as described for FIG. 8 in Example 4 above. Error bars represent standard errors for a given data set. Mean values are indicated in FIG. 10 above off-scale bars as necessary. The number of animals in each group is as indicated in FIG. 10.

Example 7

Nasal Administration of Formulations that Increase Antibody Fragment Delivery to Central Nervous System Tissues Nasal administration of a *Homo sapiens* derived antibody Fc fragment (hFc) to central nervous system (CNS) tissues was increased, relative to control hFc formulations, by inclusion of the compounds listed in Table 3 below in the hFc formulation.

TABLE 3

Antibody hFc formulations that increase antibody fragment delivery to central nervous system tissues, relative to control hFc formulations, in isoflurane anesthetized animals.

| Compound Identity and Quantity in PBS (pH 7.4) Diluent Based Formulations Containing 36 mg/ml hFc | | Mean Fold Increase* in Brain Delivery Efficiency of hFc after Nasal Administration of Formulation |
|---|---|---|
| Compound Identity | Quantity | |
| chitosan glutamate | 0.5% (w/v) | 6.1** (n = 23) |
| n-dodecyl-beta-D-maltopyranoside | 0.5% (w/v) | 7.6*** (n = 21) |
| n-decyl-beta-D-maltopyranoside | 0.5% (w/v) | 4.3 (n = 7) |
| propylene glycol | 10-20% (v/v) | 4.5**** (n = 13) |
| heptakis(2,6-di-O-methyl)-beta-cyclodextrin | 5% (w/v) | 3.1 (n = 8) |
| 1,2-didecanoyl-sn-glycero-3-phosphocholine | 2% (w/v) emulsion in 20% v/v soy bean oil, 2% v/v glycerol | 9.6 (n = 6) |
| sodium glycocholate hydrate | 1% (w/v) | 17.6 (n = 15) |
| taurocholic acid sodium salt hydrate | 1% (w/v) | 14 (n = 6) |
| Sodium tauroursodeoxycholate | 1% (w/v) | 4.0 (n = 6) |

*represents mean fold increase in brain delivery efficiency (DE) of nasally administered hFc relative to control formulation (PBS; pH 7.4 and 36 mg/ml hFc)
**4 studies, range 3-11 fold increase
***4 studies, range 6-9 fold increase
****10 and 20% PG, n = 6, range 4-10 fold increase
*****3 studies, range 16-19 fold increase Formulations comprising the compounds identified in Table 3 above were nasally administered to anesthetized rats using the methods described in Example 6 above; a 50 µL of bolus of each formulation was administered. Animals were perfused as described in Example 6 above. Brains, blood and other tissues were then dissected, collected, and analyzed for hFc content as described in Example 4 above.

Control hFc formulations comprised 36 mg/ml hFc in PBS at pH 7.4. The formulations described in Table 3 above contained each identified compound preparation in the quantity indicated in the Table. The purity by mass of compounds in compound preparations and their source is as indicated in Table A above. Percent (w/v) and percent (v/v) values reported herein are uncorrected for the purity by mass or volume of a given compound in a formulation. Formulations were made using PBS at pH 7.4 as the diluent and contained a final hFc concentration of 36 mg/ml.

As seen in Table 4, nasal administration of hFc formulations comprising 0.5% (w/v) chitosan glutamate, 0.5% (w/v)-n-dodecyl-beta-D-maltopyranoside, 0.5% (w/v) n-decyl-beta-D-maltopyranoside, 10% to 20% (v/v) propylene glycol, 5% (w/v) heptakis(2,6-di-O-methyl)-beta-cyclodextrin, 2% (w/v) 1,2-didecanoyl-sn-glycero-3-phosphocholine, 1% (w/v) sodium glycocholate hydrate; 1% (w/v) taurocholic acid sodium salt hydrate, or 1% (w/v) sodium tauroursodeoxycholate to isoflurane anesthetized animals resulted in hFc concentrations in CNS tissues that were increased relative to those in isoflurane anesthetized animals receiving the control hFc formulation in PBS only. Mean fold increase values and the number of animals in each study group are indicated in Table 3.

The present invention now being fully described, it will be apparent to one of ordinary skill in the art that changes and modifications can be made thereto without departing from the scope and spirit of the appended claims.

What is claimed is:

1. A method of delivering a therapeutic composition to the central nervous system of a mammal, comprising intranasally administering a therapeutically effective amount of an aqueous composition comprising a therapeutic polypeptide and a compound selected from the group consisting of: 1-O-n-dodecyl-beta-D-maltopyranoside, 1-O-n-decyl-beta-D-maltopyranoside, 1-O-n-tetradecyl-beta-D-maltopyranoside, and beta-D-fructopyranosyl-alpha-glucopyranoside monododecanoate, wherein the compound is present in the aqueous composition at a concentration between 0.125 g to 1 g per 100 ml of the aqueous composition.

2. The method of claim 1, wherein the polypeptide is absorbed across nasal epithelium.

3. The method of claim 2, wherein the polypeptide is selected from insulin, leutenizing hormone releasing (LHRH) and agonists of LHRH; nerve growth factor (NGF), brain-derived neurotrophic factor (BDNF), neurotrophin-3, neurotrophin-4/5; acidic fibroblast growth factor and basic fibroblast growth factor; ciliary neurotrophic factor, leukemia inhibitory factor, and cardiotrophin-1; transforming growth factor-beta-1-3 (TGF-betas), bone morphogenetic proteins (BMPs), growth differentiation factors 5 to 15, glial cell line-derived neurotrophic factor (GDNF), neurturin, artemin, activins and persephin; epidermal growth factor, transforming growth factor-alpha and neuregulins; insulin-like growth factor-1 (IGF-1), insulin-like growth factor-2 (IGF-2); Pituitary adenylate cyclase-activating polypeptide-27 (PACAP-27), PACAP-38, glucagons, Glucagon-like peptide-1 (GLP-1), GLP-2, growth hormone releasing factor, vasoactive intestinal peptide (VIP), peptide histidine methionine, secreting and glucose-dependent insulinotropic polypeptide; activity-dependent neurotrophic factor and platelet-derived growth factors (PDGFs).

4. The method of claim 2, wherein the polypeptide is exendin-4.

5. The method of claim 1, wherein the composition has a pH of between about 4 and 8.

6. The method of claim 1, wherein the compound is present in the aqueous composition at a concentration of 0.5 g per 100 ml of aqueous composition.

* * * * *